United States Patent
Sams et al.

(10) Patent No.: US 11,501,851 B2
(45) Date of Patent: Nov. 15, 2022

(54) METHODS AND SYSTEMS FOR DETERMINING ANCESTRAL RELATEDNESS

(71) Applicant: Embark Veterinary, Inc., Boston, MA (US)

(72) Inventors: Aaron J. Sams, Ithaca, NY (US); Samuel H. Vohr, Somerville, MA (US); Adam S. Gardner, Winchendon, MA (US); Matt Barton, Boston, MA (US); Ryan Boyko, Dorchester, MA (US); Adam R. Boyko, Ithaca, NY (US)

(73) Assignee: Embark Veterinary, Inc., Boston, MA (US)

( * ) Notice: Subject to any disclaimer, the term of this patent is extended or adjusted under 35 U.S.C. 154(b) by 0 days.

(21) Appl. No.: 17/556,055

(22) Filed: Jan. 6, 2022

(65) Prior Publication Data
US 2022/0122693 A1    Apr. 21, 2022

Related U.S. Application Data

(63) Continuation of application No. PCT/US2020/060899, filed on Nov. 17, 2020.

(60) Provisional application No. 62/936,879, filed on Nov. 18, 2019.

(51) Int. Cl.
    *G16B 20/40* (2019.01)
    *G16B 20/20* (2019.01)

(52) U.S. Cl.
    CPC .............. *G16B 20/40* (2019.02); *G16B 20/20* (2019.02)

(58) Field of Classification Search
    None
    See application file for complete search history.

(56) References Cited

U.S. PATENT DOCUMENTS

| | | |
|---|---|---|
| 6,537,213 B2 | 3/2003 | Dodds |
| 7,134,995 B2 | 11/2006 | Dodds |
| 7,729,863 B2 | 6/2010 | Ostrander et al. |
| 7,811,761 B2 | 10/2010 | Acland et al. |
| 7,865,343 B2 | 1/2011 | Dodds |
| 2003/0170665 A1 | 9/2003 | Daly et al. |
| 2005/0191731 A1 | 9/2005 | Judson et al. |
| 2006/0008815 A1 | 1/2006 | Rosenfeld et al. |
| 2006/0147962 A1 | 7/2006 | Jones et al. |
| 2006/0200320 A1 | 9/2006 | Al-Murrani |
| 2006/0235625 A1* | 10/2006 | Ostrander .............. G16B 20/40 702/20 |
| 2011/0087693 A1 | 4/2011 | Boyce |
| 2011/0129825 A1 | 6/2011 | Ketchum |
| 2015/0344959 A1 | 12/2015 | Boyko et al. |
| 2017/0220738 A1 | 8/2017 | Barber et al. |

FOREIGN PATENT DOCUMENTS

| | | |
|---|---|---|
| EP | 2212436 B1 | 4/2017 |
| WO | WO-2005040350 A2 | 5/2005 |
| WO | WO-2006026512 A2 | 3/2006 |
| WO | WO-2006094154 A2 | 9/2006 |
| WO | WO-2009134226 A1 | 11/2009 |

OTHER PUBLICATIONS

Wikipedia Identity by descent https://en.wikipedia.org/wiki/identify_by_descent accessed on Mar. 15, 2022 (Year: 2022).*
Shendure et al. Next-generation DNA sequencing Nature Biotechnology vol. 26, pp. 1135-1145 (Year: 2008).*
Leutenegger et al. Estimation of the Inbreeding Coefficient through Use of Genomic Data American Journal of Human Genetics vol. 73, pp. 516-523 (Year: 2003).*
Ciampolini et al. The use of genetic markers to estimate relationships between dogs in the course of criminal investigations BMC Research Notes vol. 10 article 414 (Year: 2017).*
"Sams, et al. "Fine-scale resolution and analysis of runs of homozygosity in domestic dogs" (2018) Biorxiv p. 1-20".
"Sams, et al. "Fine-scale resolution and analysis of runs of homozygosity in domestic dogs" (2019) G3 vol. 9, pp. 117-123".
"GITHUB≥ProjectAussie/GERMLINE: Linear Time detection of Identity by Descent (2022)".
"Gusev, et al. "Whole population, genome-wide mapping of hidden relatedness" (2009) Genome Research, 19:318-326".
"Hedrick, et al. "Measuring Relatedness between Inbred Individuals" (2015) Journal of Heredity, pp. 20-25".
"International Search Report and Written Opinion for PCT Application No. PCT/US2020/060899 dated Feb. 26, 2021".
"Loh, et al., "Reference-based phasing using the Haplotype Reference Consortium panel" (2016) Nat Genet 48(11): 1443-1448".
International Preliminary Report on Patentability for PCT Application No. PCT/US2020/060899 dated Jun. 2, 2022.

* cited by examiner

*Primary Examiner* — John S Brusca
(74) *Attorney, Agent, or Firm* — Wilson Sonsini Goodrich & Rosati

(57) ABSTRACT

The present disclosure provides methods of estimating a degree of ancestral relatedness between individuals. In an aspect, a method comprises receiving haplotype data comprising genetic markers shared among a population of individuals; dividing the haplotype data into segments based on the genetic markers; for each of the population of test individuals: (i) based on the genetic markers, matching segments of the haplotype data that are identical-by-descent between two individuals, (ii) for each of the matched segments: dividing the matched segment into discrete genomic intervals, scoring each of the discrete genomic intervals based on a degree of matching within or between the individuals, correcting the scores for consistency, and (iii) calculating a weighted sum over the discrete genomic intervals of the matched segment, based on the corrected scores and assigned weights; and (d) estimating the degree of ancestral relatedness between the individuals based on the weighted sums of the matched segments.

30 Claims, 2 Drawing Sheets

METHODS AND SYSTEMS FOR DETERMINING ANCESTRAL RELATEDNESS

CROSS-REFERENCE TO RELATED APPLICATIONS

This application is a continuation of International Application No. PCT/US2020/060899, filed Nov. 17, 2020, which claims the benefit of U.S. Provisional Application No. 62/936,879, filed Nov. 18, 2019, all of which are incorporated by reference herein in their entirety.

BACKGROUND

Small differences in DNA within populations of individuals may be responsible for much of the genetic and phenotypic variation observed between individuals. Certain identical-by-descent (IBD) haplotypes (e.g., small regions of DNA that are inherited together) that are shared by individuals may be indicative of a familial relationship between those individuals. Therefore, IBD analysis may be performed on a plurality of individuals to determine their ancestral relatedness.

SUMMARY

The present disclosure provides methods of estimating a degree of ancestral relatedness between individuals. In an aspect, a method comprises receiving haplotype data comprising genetic markers shared among a population of individuals; dividing the haplotype data into segments based on the genetic markers; for each of the population of test individuals: (i) based on the genetic markers, matching segments of the haplotype data that are identical-by-descent between two individuals, (ii) for each of the matched segments: dividing the matched segment into discrete genomic intervals, scoring each of the discrete genomic intervals based on a degree of matching within or between the individuals, correcting the scores for consistency, and (iii) calculating a weighted sum over the discrete genomic intervals of the matched segment, based on the corrected scores and assigned weights; and (d) estimating the degree of ancestral relatedness between the individuals based on the weighted sums of the matched segments.

In an aspect, the present disclosure provides a computer-implemented method for estimating a degree of ancestral relatedness between two individuals of a diploid population, comprising: (a) receiving haplotype data for a population of test individuals, the haplotype data comprising a plurality of genetic markers shared among the population of test individuals; (b) dividing the haplotype data into segments based on the plurality of genetic markers; (c) for each of the population of test individuals: (i) based on the plurality of genetic markers, matching segments of the haplotype data that are identical-by-descent between a first individual and a second individual among the population of test individuals, each of the matched segments having a first size that is at least a pre-determined threshold size and comprising at least a pre-determined number of genetic markers; (ii) for each of the matched segments between the first individual and the second individual: dividing the matched segment into a plurality of discrete genomic intervals; scoring each of the plurality of discrete genomic intervals based on (i) a degree of homozygosity matching of the discrete genomic interval within the first individual or the second individual or (ii) a degree of pairwise matching of the discrete genomic interval between the first individual and the second individual, thereby generating a plurality of scores; correcting the plurality of scores based on a consistency of the plurality of scores, thereby producing a plurality of corrected scores; and assigning a plurality of weights to the plurality of discrete genomic intervals, based on the plurality of corrected scores of the discrete genomic intervals; and (iii) calculating a weighted sum over the plurality of discrete genomic intervals of the matched segment, based on the plurality of corrected scores and the plurality of weights; and (d) estimating the degree of ancestral relatedness between the first individual and the second individual based on the weighted sums of the matched segments.

In some embodiments, the diploid population is a mammal population. In some embodiments, the mammal population is a canine population, a feline population, a sport animal population, or a rodent population. In some embodiments, the mammal population is a canine population. In some embodiments, the canine population is a dog population. In some embodiments, the mammal population is a feline population. In some embodiments, the feline population is a cat population. In some embodiments, the mammal population is a sport animal population. In some embodiments, the sport animal population is a horse population. In some embodiments, the dog population comprises one or more dog breeds selected from the group consisting of. Affenpinscher, Afghan Hound, Africanis, Aidi, Airedale Terrier, Akbash Dog, Akita Inu, Alangu Mastiff, Alano Español, Alapaha Blue Blood Bulldog, Alaskan Klee Kai, Alaskan Malamute, Alaunt, Alopekis, Alpine Dachsbracke, Alsatian Shepalute, American Akita, American Bulldog, American Cocker Spaniel, American Eskimo Dog, American Foxhound, American Hairless Terrier, American Mastiff, American Pit Bull Terrier, American Staffordshire Terrier, American Water Spaniel, Anatolian Shepherd Dog, Anglo-Français de Petite Vénerie, Appenzeller Sennenhund, Argentine Dogo, Ariege Pointer, Ariegeois, Armant, Artois Hound, Australian Bulldog, Australian Cattle Dog, Australian Kelpie, Australian Shepherd, Australian Silky Terrier, Australian Stumpy Tail Cattle Dog, Australian Terrier, Austrian Black and Tan Hound, Austrian Pinscher, Azawakh, Bakharwal Dog, Barbet, Basenji, Basque Shepherd Dog, Basset Artésien Normand, Basset Bleu de Gascogne, Basset Fauve de Bretagne, Grand Basset Griffon Vendéen, Petit Basset Griffon Vendéen, Bavarian Mountain Hound, Beagle, Beagle-Harrier, Bearded Collie, Beauceron, Bedlington Terrier, Belgian Shepherd Dog, Belgian Shepherd Dog (Groenendael), Belgian Shepherd Dog (Laekenois), Belgian Shepherd Dog (Malinois), Belgian Shepherd (Tervuren), Bergamasco Shepherd, Berger Blanc Suisse, Berger Picard, Berner Laufhund, Bernese Mountain Dog, Bichon Frisé, Billy, Bisben, Black and Tan Coonhound, Black and Tan Virginia Foxhound, Bullenbeisser, Black Norwegian Elkhound, Black Russian Terrier, Blackmouth Cur, Grand Bleu de Gascogne, Petit Bleu de Gascogne, Bloodhound, Blue Lacy, Blue Paul Terrier, Bluetick Coonhound, Boerboel, Bohemian Shepherd, Bolognese, Border Collie, Border Terrier, Borzoi, Bosnian Coarse-haired Hound, Boston Terrier, Bouvier des Ardennes, Bouvier des Flandres, Boxer, Boykin Spaniel, Bracco Italiano, Braque d'Auvergne, Braque du Bourbonnais, Braque du Puy, Braque Francais, Braque Saint-Germain, Brazilian Terrier, Briard, Briquet Griffon Vendéen, Brittany, Broholmer, Bruno Jura Hound, Bucovina Shepherd Dog, Bull and Terrier, Bull Terrier, Bull Terrier (Miniature), Bullmastiff, Bully Kutta, Cairn Terrier, Canaan Dog, Canadian Eskimo Dog, Canadian Pointer, Cane Corso, Cão da Serra de Aires, Cão de Castro Laboreiro, Cão Fila de Sao Miguel, Carolina Dog, Carpathian Shepherd Dog, Catahoula Cur, Catalan Sheepdog, Caucasian Shepherd Dog, Cavalier King Charles Spaniel, Central Asian Shepherd Dog, Cesky Fousek, Cesky Terrier, Polish Greyhound, Chesapeake Bay Retriever, Chien-gris, Chien Français Blanc et Noir, Chien Français Blanc et Orange, Chien Français Tricolore, Chihuahua, Chilean Fox Terrier, Chinese Chongqing Dog, Chinese Crested Dog, Chinese Imperial Dog, Chinook, Chippiparai, Chow Chow, Cimarrón Uruguayo, Cierny Sery, Cimeco dell'Etna, Clumber Spaniel, Rough Collie, Smooth Collie, Combai, Cordoba Fighting Dog, Coton de Tulear, Cretan Hound, Croatian Sheepdog, Cumberland Sheepdog, Curly Coated Retriever, Czechoslovakian Wolfdog, Dachshund, Dalmatian, Dandie Dinmont Terrier, Danish Swedish Farmdog, Dingo, Doberman Pinscher, Dogue de Bordeaux, Dogo Cubano, Dogo Guatemalteco, Dogo Sardesco, Drentse Patrijshond, Drever, Dunker, Dutch Shepherd Dog, Dutch Smoushond, East-European Shepherd, East Siberian Laika, Elo, English Cocker Spaniel, English Coonhound, English Foxhound, English Mastiff, English Pointer, English Setter, English Shepherd, English Springer Spaniel, English Toy Terrier (Black & Tan), English Water Spaniel, English White Terrier, Entlebucher Mountain Dog, Épagneul Bleu de Picardie, Estonian Hound, Estrela Mountain Dog, Eurasier, Field Spaniel, Fila Brasileiro, Findo, Finnish Hound, Finnish Lapphund, Finnish Spitz, Flat-Coated Retriever, Formosan Mountain Dog, Fox Terrier (Smooth), Wire Fox Terrier, French Brittany, French Bulldog, French Spaniel, Galgo Español, German Longhaired Pointer, German Pinscher, German Shepherd Dog, German Shorthaired Pointer, German Spaniel, German Spitz, German Wirehaired Pointer, Giant Schnauzer, Glen of Imaal Terrier, Golden Retriever, Gordon Setter, Grand Anglo-Français Blanc et Noir, Grand Anglo-Français Blanc et Orange, Grand Anglo-Français Tricolore, Grand Griffon Vendéen, Gran Mastin de Borínquen, Great Dane, Great Pyrenees, Greater Swiss Mountain Dog, Greenland Dog, Greyhound, Griffon Bleu de Gascogne, Griffon Bruxellois, Griffon Fauve de Bretagne, Griffon Nivemais, Gull Dong, Gull Terr, Hare Indian Dog, Hamiltonstövare, Hanover Hound, Harrier, Havanese, Hawaiian Poi Dog, Himalayan Sheepdog, Hokkaido, Hortaya Borzaya, Hovawart, Hungarian Hound, New Zealand Huntaway, Hygenhund, Ibizan Hound, Icelandic Sheepdog, Indian Spitz, Irish Bull Terrier, Irish Red and White Setter, Irish Setter, Irish Staffordshire Bull Terrier, Irish Terrier, Irish Water Spaniel, Irish Wolfhound, Istrian Shorthaired Hound, Istrian Coarse-haired Hound, Italian Greyhound, Jack Russell Terrier, Jagdterrier, Jämthund, Japanese Chin, Japanese Spitz, Japanese Terrier, Jonangi, Kaikadi, Kai Ken, Kangal Dog, Kanni, Karakachan Dog, Karelian Bear Dog, Karst Shepherd, Keeshond, Kerry Beagle, Kerry Blue Terrier, King Charles Spaniel, King Shepherd, Kintamani, Kishu, Komondor, Kooikerhondje, Koolie, Korean Jindo Dog, Korean Mastiff, Kromfohrländer, Kunming Wolf-dog, Kuri, Kuvasz, Kyi-Leo, Labrador Husky, Labrador Retriever, Lagotto Romagnolo, Lakeland Terrier, Lancashire Heeler, Landseer, Lapponian Herder, Leonberger, Lhasa Apso, Lithuanian Hound, Longhaired Whippet, Lottatore Brindisino, Löwchen, Magyar Agár, Majestic Tree Hound, Maltese, Manchester Terrier, Maremma Sheepdog, McNab, Mexican Hairless Dog, Miniature Australian Shepherd, Miniature Fox Terrier, Miniature Pinscher, Miniature Schnauzer, Miniature Siberian Husky, Mioritic, Molossus, Montenegrin Mountain Hound, Moscow Watchdog, Moscow Water Dog, Mountain Cur, Mountain View Cur, Mucuchies, Mudi, Mudhol Hound, Large Münsterländer, Small Münsterländer, Murray River Curly Coated Retriever, Neapolitan Mastiff, Newfoundland, New Guinea Singing Dog, Norfolk Spaniel, Norfolk Terrier, Norrbottenspets, North Country Beagle, Northern Inuit Dog, Norwegian Buhund, Norwegian Elkhound, Norwegian Lundehund, Norwich Terrier, Nova Scotia Duck-Tolling Retriever, Old Danish Pointer, Old English Sheepdog, Old English Bulldog, Old English Terrier, Old German Shepherd Dog, Olde English Bulldogge, Otterhound, Pachon Navarro, Paisley Terrier, Papillon, Parson Russell Terrier, Patterdale Terrier, Pekingese, Perro de Presa Canario, Perro de Presa Mallorquin, Peruvian Hairless Dog, Phaléne, Pharaoh Hound, Picardy Spaniel, Plott Hound, Podenco Canario, Pointer, Polish Hound, Polish Hunting Dog, Polish Lowland Sheepdog, Polish Tatra Sheepdog, Pomeranian, Pont-Audemer Spaniel, Poodle, Porcelaine, Portuguese Podengo, Portuguese Pointer, Portuguese Water Dog, Pražský Krysarík, Pudelpointer, Pug, Puli, Pumi, Pungsan Dog, Pyrenean Mastiff, Pyrenean Shepherd, Rafeiro do Alentejo, Rajapalayam, Rampur Greyhound, Rastreador Brasileiro, Ratonero Bodeguero Andaluz, Rat Terrier, Redbone Coonhound, Rhodesian Ridgeback, Rottweiler, Russian Spaniel, Russkiy Toy, Russo-European Laika, Russell Terrier, Saarlooswolfhond, Sabueso Espanol, Sage Ashayeri, Sage Mazandarani, Sakhalin Husky, Saluki, Samoyed, Sapsali, Šarplaninac, Schapendoes, Schillerstövare, Schipperke, Old Croatian Sighthound, Giant Schnauzer, Miniature Schnauzer, Standard Schnauzer, Schweizer Laufhund, Schweizerischer Niederlaufhund, Scotch Collie, Scottish Deerhound, Scottish Terrier, Sealyham Terrier, Segugio Italiano, Seppala Siberian Sleddog, Serbian Hound, Serbian Tricolour Hound, Shar Pei, Shetland Sheepdog, Shiba Inu, Shih Tzu, Shikoku, Shiloh Shepherd Dog, Shirak, Siberian Husky, Silken Windhound, Sinhala Hound, Skye Terrier, Sloughi, Slovak Cuvac, Slovakian Rough-haired Pointer, Slovenský Kopov, Smålandsstövare, Small Greek Domestic Dog, Soft-Coated Wheaten Terrier, South Russian Ovcharka, Southern Hound, Spanish Mastiff, Spanish Water Dog, Spinone Italiano, Sporting Lucas Terrier, St. Bernard, St. John's Water Dog, Stabyhoun, Staffordshire Bull Terrier, Stephens Cur, Styrian Coarse-haired Hound, Sussex Spaniel, Swedish Lapphund, Swedish Vallhund, Swedish Beagle, Tahltan Bear Dog, Taigan, Tamaskan Dog, Teddy Roosevelt Terrier, Telomian, Tenterfield Terrier, Thai Bangkaew Dog, Thai Ridgeback, Tibetan Mastiff, Tibetan Spaniel, Tibetan Terrier, Tomjak, Tosa, Toy Bulldog, Toy Fox Terrier, Toy Manchester Terrier, Treeing Cur, Treeing Walker Coonhound, Tyrolean Hound, Utonagan, Vizsla, Volpino Italiano, Weimaraner, Cardigan Welsh Corgi, Pembroke Welsh Corgi, Welsh Sheepdog, Welsh Springer Spaniel, Welsh Terrier, West Highland White Terrier, West Siberian Laika, Westphalian Dachsbracke, Wetterhoun, Whippet, White English Bulldog, White Shepherd Dog, Wirehaired Vizsla, Wirehaired Pointing Griffon, and Yorkshire Terrier. In some embodiments, the population comprises one or more purebred dogs (e.g., having a single breed type) or one or more mixed-breed dogs (e.g., having a plurality of breed types). In some embodiments, the population is a population of mixed-breed dogs having DNA from any number (e.g., 1, 2, 3, 4, 5, 6, 7, 8, 9, 10, or more than 10) or combination of the purebred dogs.

In some embodiments, the haplotype data is generated by processing genotype data of the population of test individuals using a haplotype phasing algorithm. In some embodiments, the haplotype phasing algorithm comprises a reference-based haplotype phasing algorithm. In some embodiments, the reference-based haplotype phasing algorithm comprises a Hidden Markov Model (HMM)-based search. In some embodiments, the reference-based haplotype phasing algorithm comprises an Eagle1 algorithm, an Eagle2 algorithm, a PHASE algorithm, a fastPHASE algorithm, a BEAGLE algorithm, a Findhap algorithm, an Impute algorithm, an FImpute algorithm, an AlphaImpute algorithm, an IMPUTE2 algorithm, a MaCH algorithm, a SHAPEIT1 algorithm, a SHAPEIT2 algorithm, a SHAPEIT3 algorithm, a SHAPEIT4 algorithm, or a combination thereof. In some embodiments, the haplotype phasing algorithm comprises a cohort-based haplotype phasing algorithm.

In some embodiments, the genotype data is obtained by assaying biological samples obtained from the population of test individuals. In some embodiments, the biological samples comprise blood samples, saliva samples, swab samples, cell samples, or tissue samples. In some embodiments, the assaying comprises sequencing the biological samples or derivatives thereof.

In some embodiments, the plurality of genetic markers comprises at least about 500, at least about 1,000, at least about 2,000, at least about 3,000, at least about 4,000, at least about 5,000, at least about 6,000, at least about 7,000, at least about 8,000, at least about 9,000, or at least about 10,000 distinct genetic markers.

In some embodiments, matching the segments of the haplotype data that are identical-by-descent comprises using a GERMLINE algorithm, a PLINK algorithm, a PREST algorithm, a Random Projection for IBD Detection (RaPID) algorithm, a Find IBD Shared Haplotypes Rapidly (FISHR) algorithm, a refined identical-by-descent (IBD) algorithm, a fastIBD algorithm, a KING algorithm, a HaploScore algorithm, a TRUFFLE algorithm, or a combination thereof. In some embodiments, the pre-determined threshold size is about 100 kilobase pairs (kbp), about 200 kbp, about 300 kbp, about 400 kbp, about 500 kbp, about 600 kbp, about 700 kbp, about 800 kbp, about 900 kbp, or about 1,000 kbp. In some embodiments, the pre-determined number of genetic markers is about 30, about 40, about 50, about 60, about 70, about 80, about 90, or about 100 distinct genetic markers.

In some embodiments, the method further comprises dividing the matched segments such that the discrete genomic intervals of the plurality of discrete genomic intervals have an equal size. In some embodiments, the method further comprises dividing the matched segments such that the discrete genomic intervals of the plurality of discrete genomic intervals have a variable size. In some embodiments, the variable size of a given discrete genomic interval of the plurality of discrete genomic intervals is determined based at least in part on a start position and an end position of IBD matches proximal to the given discrete genomic interval, a density of genetic markers in the given discrete genomic interval, a maximum number of markers for the given discrete genomic interval, a maximum length of the given discrete genomic interval, or a combination thereof.

In some embodiments, the method further comprises scoring each of the plurality of discrete genomic intervals based on (i) the degree of homozygosity matching of the discrete genomic interval within the first individual or the second individual and (ii) the degree of pairwise matching of the discrete genomic interval between the first individual and the second individual, thereby generating a plurality of homozygosity matching scores and a plurality of pairwise matching scores. In some embodiments, the method further comprises correcting the plurality of pairwise matching scores based on a consistency of a given pairwise matching score with a corresponding homozygosity matching score, thereby producing a plurality of corrected pairwise matching scores.

In some embodiments, the method further comprises assigning the plurality of weights to the plurality of discrete genomic intervals, based on a plurality of identity states for two alleles in two diploid individuals. In some embodiments, the plurality of identity states comprises identity states selected from Table 1, and the plurality of weights are assigned based on a plurality of contributions to relatedness $r_{xy}$ as listed in Table 1. In some embodiments, the degree of ancestral relatedness comprises a coefficient of relatedness. In some embodiments, the method further comprises calculating the weighted sum over the plurality of discrete genomic intervals of the matched segment, wherein the weighted sum is expressed by:

$$r_{xy} = \frac{\Delta 1 + \Delta 7 + (0.75 \times \Delta 3) + (0.5 \times \Delta 8)}{L}.$$

In some embodiments, the degree of ancestral relatedness comprises a coefficient of kinship. In some embodiments, the method further comprises calculating the weighted sum over the plurality of discrete genomic intervals of the matched segment, wherein the weighted sum is expressed by:

$$k_{xy} = \frac{\Delta 1 + (0.5 \times (\Delta 3 + \Delta 7)) + (0.25 \times \Delta 8)}{L}.$$

In some embodiments, estimating the degree of ancestral relatedness between the first individual and the second individual comprises determining a degree of inbreeding of the first individual or the second individual. In some embodiments, estimating the degree of ancestral relatedness between the first individual and the second individual comprises determining a degree of inbreeding of the first individual and the second individual. In some embodiments, the method further comprises determining a familial relationship between the first individual and the second individual based at least in part on the degree of inbreeding of the first individual and the second individual. In some embodiments, the familial relationship is a parent-child relationship, a sibling relationship, an aunt/uncle-nephew/niece relationship, a cousin relationship, a grandparent-grandchild relationship, or a great-grandparent-greatgrandchild relationship. In some embodiments, the familial relationship is given as a relationship between a pair of humans, such that the degree of ancestral relatedness between the first individual and the second individual is comparable to a degree of ancestral relatedness expected between the pair of humans. In some embodiments, the relationship is a parent-child relationship, a sibling relationship, an aunt/uncle-nephew/niece relationship, a cousin relationship, a grandparent-grandchild relationship, or a great-grandparent-greatgrandchild relationship.

In some embodiments, the method further comprises determining an expected degree of inbreeding of a potential offspring of the first individual and the second individual. In some embodiments, the method further comprises determining a recommendation indicative of whether or not to breed the first individual and the second individual together, based on the expected degree of inbreeding of the potential offspring of the first individual and the second individual. In some embodiments, the method further comprises determining a recommendation indicative of breeding the first individual and the second individual together, when the expected degree of inbreeding of the potential offspring of the first individual and the second individual does not exceed a pre-determined threshold degree of inbreeding. In some embodiments, the method further comprises determining a recommendation indicative of not breeding the first individual and the second individual together, when the expected degree of inbreeding of the potential offspring of the first individual and the second individual exceeds a pre-determined threshold degree of inbreeding. In some embodiments, the pre-determined threshold degree of inbreeding is about 0.10, about 0.15, about 0.20, about 0.25, about 0.30, about 0.35, about 0.40, about 0.45, or about 0.50.

In some embodiments, the method further comprises generating a social connection between a first person associated with the first individual and a second person associated with the second individual, based at least in part on the estimated degree of ancestral relatedness between the first individual and the second individual. In some embodiments, the social connection is generated when the estimated degree of ancestral relatedness between the first individual and the second individual exceeds a pre-determined threshold value. In some embodiments, the pre-determined threshold value is about 0.00001, about 0.0001, about 0.001, about 0.01, about 0.02, about 0.04, about 0.06, about 0.08, about 0.1, about 0.12, about 0.14, about 0.16, about 0.18, about 0.2, about 0.25, about 0.3, about 0.35, about 0.4, about 0.45, or about 0.5. In some embodiments, the social connection is generated through a social media network. In some embodiments, the first person is a pet owner of the first individual, and the second person is a pet owner of the second individual. In some embodiments, the same person is a pet owner of the first individual and the second individual. In some embodiments, generating the social connection between the first person and the second person comprises providing a location of the first person or the second person. In some embodiments, generating the social connection between the first person and the second person comprises providing a communication link between the first person and the second person In some embodiments, the method further comprises identifying a familial relationship between the first individual and the second individual based at least in part on the degree of ancestral relatedness. In some embodiments, the familial relationship is a parent-child relationship, a sibling relationship, an aunt/uncle-nephew/niece relationship, a cousin relationship, a grandparent-grandchild relationship, or a great-grandparent-greatgrandchild relationship. In some embodiments, the familial relationship is given as a relationship between a pair of humans, such that the degree of ancestral relatedness between the first individual and the second individual is comparable to a degree of ancestral relatedness expected between the pair of humans. In some embodiments, the relationship is a parent-child relationship, a sibling relationship, an aunt/uncle-nephew/niece relationship, a cousin relationship, a grandparent-grandchild relationship, or a great-grandparent-greatgrandchild relationship.

In some embodiments, the method further comprises identifying, for each of one or more individuals of the population of test individuals, a presence, an absence, a risk, or a carrier status of a genetic or health condition in the individual. In some embodiments, the genetic or health condition is selected from the group consisting of Thrombopathia (RASGRP2 Exon 8); Pyruvate Kinase Deficiency (PKLR Exon 7 Pug Variant); Factor IX Deficiency, Hemophilia B (F9 Exon 7, Terrier Variant); Pyruvate Kinase Deficiency (PKLR Exon 7 Beagle Variant); P2Y12 Receptor Platelet Disorder (P2RY12); Glanzmann's Thrombasthenia Type I (ITGA2B Exon 12); Von Willebrand Disease Type II, Type II vWD (VWF); May-Hegglin Anomaly (MYH9); Thrombopathia (RASGRP2 Exon 5, American Eskimo Dog Variant); Factor IX Deficiency, Hemophilia B (F9 Exon 7, Rhodesian Ridgeback Variant); Von Willebrand Disease Type I (VWF); Canine Elliptocytosis (SPTB Exon 30); Canine Leukocyte Adhesion Deficiency Type III, LAD3 (FERMT3); Prekallikrein Deficiency (KLKB1 Exon 8); Von Willebrand Disease Type III, Type III vWD (VWF Exon 4); Factor VIII Deficiency, Hemophilia A (F8 Exon 10, Boxer Variant); Trapped Neutrophil Syndrome (VPS13B); Pyruvate Kinase Deficiency (PKLR Exon 7 Labrador Variant); Thrombopathia (RASGRP2 Exon 5, Basset Hound Variant); Pyruvate Kinase Deficiency (PKLR Exon 5); Factor VIII Deficiency, Hemophilia A (F8 Exon 1, Shepherd Variant 2); Factor VII Deficiency (F7 Exon 5); Congenital Macrothrombocytopenia (TUBB1 Exon 1, Cavalier King Charles Spaniel Variant); Ligneous Membranitis, LM (PLG); Pyruvate Kinase Deficiency (PKLR Exon 10); Factor VIII Deficiency, Hemophilia A (F8 Exon 11, Shepherd Variant 1); Other Systems; Shar-Pei Autoinflammatory Disease, SPAID, Shar-Pei Fever (MTBP); Autosomal Recessive Amelogenesis Imperfecta, Familial Enamel Hypoplasia (Italian Greyhound Variant); Persistent Mullerian Duct Syndrome, PMDS (AMHR2); Deafness and Vestibular Syndrome of Dobermans, DVDob, DINGS; Eyes; Progressive Retinal Atrophy, crd2 (IQCB1); Primary Lens Luxation (ADAMTS17); Glaucoma Primary Open Angle Glaucoma (ADAMTS17 Exon 2); Progressive Retinal Atrophy, crd1 (PDE6B); Progressive Retinal Atrophy, rcd1 Rod-cone dysplasia, rcd1 (PDE6B Exon 21 Irish Setter Variant); Collie Eye Anomaly, Choroidal Hypoplasia, CEA (NHEJ1); Progressive Retinal Atrophy (SAG); Achromatopsia (CNGA3 Exon 7 German Shepherd Variant); Canine Multifocal Retinopathy cmr2 (BEST1 Exon 5); Glaucoma Primary Open Angle Glaucoma (ADAMTS17 Exon 11); Progressive Retinal Atrophy, prcd Progressive rod-cone degeneration (PRCD Exon 1); Hereditary Cataracts, Early-Onset Cataracts, Juvenile Cataracts (HSF4 Exon 9 Shepherd Variant); Autosomal Dominant Progressive Retinal Atrophy (RHO); Canine Multifocal Retinopathy cmr3 (BEST1 Exon 10 SNP); Achromatopsia (CNGA3 Exon 7 Labrador Retriever Variant); Canine Multifocal Retinopathy cmr1 (BEST1 Exon 2); Progressive Retinal Atrophy, rcd3 Rod-cone dysplasia, rcd3 (PDE6A); Progressive Retinal Atrophy (CNGB1); Golden Retriever Progressive Retinal Atrophy 2, GR-PRA2 (TTC8); Progressive Retinal Atrophy, CNGA (CNGA1 Exon 9); Golden Retriever Progressive Retinal Atrophy 1, GR-PRA1 (SLC4A3); Progressive Retinal Atrophy—crd4/cord1 (RPGRIP1); Congenital Stationary Night Blindness (RPE65); Macular Corneal Dystrophy, MCD (CHST6); Glaucoma Primary Open Angle Glaucoma (ADAMTS10 Exon 9); Canine Multifocal Retinopathy cmr3 (BEST1 Exon 10 Deletion); Glaucoma Primary Open Angle Glaucoma (ADAMTS10 Exon 17); Muscular; Centronuclear Myopathy (PTPLA); Myotonia Congenita (CLCN1 Exon 7); Inherited Myopathy of Great Danes (BIN1); Myotonia Congenita (CLCN1 Exon 23); Muscular Dystrophy Muscular Dystrophy (DMD Pembroke Welsh Corgi Variant); Exercise-Induced Collapse (DNM1); Muscular Dystrophy Muscular Dystrophy (DMD Golden Retriever Variant); Myostatin Deficiency, Bully Whippet Syndrome (MSTN); Myotubular Myopathy 1, X-linked Myotubular Myopathy, XL-MTM (MTM1, Labrador Variant); Muscular Dystrophy Cavalier King Charles Spaniel Variant 1; Multisystem; Primary Ciliary Dyskinesia, PCD (CCDC39 Exon 3); GM1 Gangliosidosis (GLB1 Exon 2); Mucopolysaccharidosis Type IIIA, Sanfilippo Syndrome Type A, MPS IIIA (SGSH Exon 6 Variant 1); Adult-Onset Neuronal Ceroid Lipofuscinosis (ATP13A2); GM1 Gangliosidosis (GLB1 Exon 15 Shiba Inu Variant); Neuronal Ceroid Lipofuscinosis 2, NCL 2 (TPP1 Exon 4); Mucopolysaccharidosis Type VII, Sly Syndrome, MPS VII (GUSB Exon 3); Canine Fucosidosis (FUCA1); GM1 Gangliosidosis (GLB1 Exon 15 Alaskan Husky Variant); Lagotto Storage Disease (ATG4D); Congenital Keratoconjunctivitis Sicca and Ichthyosiform Dermatosis, Dry Eye Curly Coat Syndrome, CKCSID (FAM83H Exon 5); Glycogen storage disease Type VII, Phosphofructokinase Deficiency, PFK Deficiency (PFKM Whippet and English Springer Spaniel Variant); Glycogen Storage Disease Type IA, Von Gierke Disease, GSD IA (G6PC); Glycogen storage disease Type VII, Phosphofructokinase Deficiency, PFK Deficiency (PFKM Wachtelhund Variant); Neuronal Ceroid Lipofuscinosis 1, NCL 1 (CLN5 Border Collie Variant); Neuronal Ceroid Lipofuscinosis 1, Cerebellar Ataxia, NCL-A (ARSG Exon 2); Neuronal Ceroid Lipofuscinosis 6, NCL 6 (CLN6 Exon 7); Mucopolysaccharidosis Type I, MPS I (IDUA); Renal Cystadenocarcinoma and Nodular Dermatofibrosis, RCND (FLCN Exon 7); Neuronal Ceroid Lipofuscinosis 10, NCL 10 (CTSD Exon 5); Globoid Cell Leukodystrophy, Krabbe disease (GALC Exon 5); Glycogen Storage Disease Type IIIA, GSD IIIA (AGL); Neuronal Ceroid Lipofuscinosis (MFSD8); GM2 Gangliosidosis (HEXB, Poodle Variant); X-linked Ectodermal Dysplasia, Anhidrotic Ectodermal Dysplasia (EDA Intron 8); Neuronal Ceroid Lipofuscinosis (CLN8 Australian Shepherd Variant); Neuronal Ceroid Lipofuscinosis 8, NCL 8 (CLN8 English Setter Variant); Neuronal Ceroid Lipofuscinosis 1, NCL 1 (PPT1 Exon 8); Neuronal Ceroid Lipofuscinosis (CLN5 Golden Retriever Variant); Mucopolysaccharidosis Type VII, Sly Syndrome, MPS VII (GUSB Exon 5); Glycogen Storage Disease Type II, Pompe's Disease, GSD II (GAA); GM2 Gangliosidosis (HEXA); Mucopolysaccharidosis Type IIIA, Sanfilippo Syndrome Type A, MPS IIIA (SGSH Exon 6 Variant 2); Skin & Connective Tissues; Ichthyosis (PNPLA1); Ichthyosis (SLC27A4); Dystrophic Epidermolysis Bullosa (COL7A1); Ichthyosis, Epidermolytic Hyperkeratosis (KRT10); Ectodermal Dysplasia, Skin Fragility Syndrome (PKP1); Ichthyosis (NIPAL4); Musladin-Lueke Syndrome (AD-AMTSL2); Focal Non-Epidermolytic Palmoplantar Keratoderma, Pachyonychia Congenita (KRT16); Hereditary Nasal Parakeratosis (SUV39H2); Hereditary Footpad Hyperkeratosis (FAM83G); Brain and Spinal Cord; Juvenile-Onset Polyneuropathy, Leonberger Polyneuropathy 1, LPN1 (LPN1, ARHGEF10); Cerebellar Abiotrophy, Neonatal Cerebellar Cortical Degeneration, NCCD (SPTBN2); Narcolepsy (HCRTR2 Intron 6); L-2-Hydroxyglutaricaciduria, L2HGA (L2HGDH); Spongy Degeneration with Cerebellar Ataxia 2, SDCA2 (ATP1B2); Progressive Neuronal Abiotrophy, Canine Multiple System Degeneration, CMSD (SERACI Exon 15); Fetal-Onset Neonatal Neuroaxonal Dystrophy (MFN2); Neonatal Encephalopathy with Seizures, NEWS (ATF2); Benign Familial Juvenile Epilepsy, Remitting Focal Epilepsy (LGI2); Juvenile Laryngeal Paralysis and Polyneuropathy, Polyneuropathy with Ocular Abnormalities and Neuronal Vacuolation, POANV (RAB3GAP1, Rottweiler Variant); Progressive Neuronal Abiotrophy, Canine Multiple System Degeneration, CMSD (SERACI Exon 4); Cerebellar Ataxia, Progressive Early-Onset Cerebellar Ataxia (SEL1L); Hereditary Sensory Autonomic Neuropathy, Acral Mutilation Syndrome, AMS (GDNF-AS); Shaking Puppy Syndrome, X-linked Generalized Tremor Syndrome (PLP); Hypomyelination and Tremors (FNIP2); Spinocerebellar Ataxia, Late-Onset Ataxia, LoSCA (CAPN1); Polyneuropathy, NDRG1 Greyhound Variant (NDRG1 Exon 15); Polyneuropathy, NDRG1 Malamute Variant (NDRG1 Exon 4); Cerebellar Hypoplasia (VLDLR); Spongy Degeneration with Cerebellar Ataxia 1, SDCA1, SeSAME/EAST Syndrome (KCNJ10); Spinocerebellar Ataxia with Myokymia and/or Seizures (KCNJ10); Alaskan Husky Encephalopathy, Subacute Necrotizing Encephalomyelopathy (SLC19A3); Degenerative Myelopathy, DM (SOD1A); Alexander Disease (GFAP); Heart; Dilated Cardiomyopathy, DCM1 (PDK4); Long QT Syndrome (KCNQ1); Dilated Cardiomyopathy, DCM2 (TTN); Skeletal; Hereditary Vitamin D-Resistant Rickets (VDR); Osteogenesis Imperfecta, Brittle Bone Disease (COL1A1); Osteogenesis Imperfecta, Brittle Bone Disease (SERPINHI); Chondrodystrophy and Intervertebral Disc Disease, CDDY/IVDD, Type I IVDD (FGF4 retrogene—CFA12); Osteogenesis Imperfecta, Brittle Bone Disease (COL1A2); Craniomandibular Osteopathy, CMO (SLC37A2); Skeletal Dysplasia 2, SD2 (COL11A2); Cleft Lip and/or Cleft Palate (ADAMTS20); Oculoskeletal Dysplasia 1, Dwarfism-Retinal Dysplasia, OSD1 (COL9A3, Labrador Retriever); Osteochondrodysplasia, Skeletal Dwarfism (SLC13A1); Metabolic; Malignant Hyperthermia (RYRI); Hypocatalasia, Acatalasemia (CAT); Pyruvate Dehydrogenase Deficiency (PDP1); Kidney and Bladder; Hyperuricosuria and Hyperuricemia or Urolithiasis, HUU (SLC2A9); Polycystic Kidney Disease, PKD (PKD1); Protein Losing Nephropathy, PLN (NPHS1); Cystinuria Type II-A (SLC3A1); Primary Hyperoxaluria (AGXT); Cystinuria Type I-A (SLC3A1); Autosomal Recessive Hereditary Nephropathy, Familial Nephropathy, ARHN (COL4A4 Exon 3); X-Linked Hereditary Nephropathy, XLHN (COL4A5 Exon 35, Samoyed Variant 2); Cystinuria Type II-B (SLC7A9); 2,8-Dihydroxyadenine Urolithiasis, 2,8-DHA Urolithiasis (APRT); Neuromuscular; Episodic Falling Syndrome (BCAN); Congenital Myasthenic Syndrome (COLQ); Congenital Myasthenic Syndrome (CHAT); Immune; Severe Combined Immunodeficiency (RAG1); X-linked Severe Combined Immunodeficiency (IL2RG Variant 1); Severe Combined Immunodeficiency (PRKDC); X-linked Severe Combined Immunodeficiency (IL2RG Variant 2); Complement 3 Deficiency, C3 Deficiency (C3); Gastrointestinal; Imerslund-Grasbeck Syndrome, Selective Cobalamin Malabsorption (CUBN Exon 53); Imerslund-Grasbeck Syndrome, Selective Cobalamin Malabsorption (CUBN Exon 8); Clinical; MDR1 Drug Sensitivity (MDR1); Alanine Aminotransferase Activity (GPT); Hormones; and Congenital Hypothyroidism (TPO, Tenterfield Terrier Variant). In some embodiments, the risk is expressed as a probability or a relative risk of the individual having the genetic or health condition. In some embodiments, the relative risk is a numerical value (e.g., a relative risk ratio) or a categorical value (e.g., "at risk," "not at risk," or "clear"). In some embodiments, the carrier status is expressed as a positive or negative indication of the individual being a carrier of the genetic or health condition.

In some embodiments, the method further comprises identifying, for each of one or more individuals of the population of test individuals, one or more dog breeds of the individual. In some embodiments, the method further comprises identifying, for each of one or more individuals of the population of test individuals, one or more proportions of the one or more dog breeds of the individual. In some embodiments, the method further comprises generating a family tree of a plurality of individuals of the population of test individuals. In some embodiments, the method further comprises identifying, for each of one or more individuals of the population of test individuals, a presence, absence, or risk of a phenotype or trait in the individual. In some embodiments, the phenotype or trait is selected from the group consisting of: base coat color (e.g., dark or light fur, color of pigment, and color dilution), color coat modifiers (e.g., hidden patterning, body pattern, and facial pattern), coat traits (e.g., furnishings, coat length, shedding, coat texture, hairlessness (Xolo type), hairlessness (Terrier type), and albinism), body features (e.g., muzzle length, tail length, hind dew claws, back muscling and bulk, and eye color), body size (e.g., smaller, intermediate, and larger), performance (e.g., altitude adaptation), genetic diversity (e.g., degree of inbreeding, and diversity in immune response).

In some embodiments, the method further comprises generating a report indicative of one or more of: the degree of ancestral relatedness; the familial relationship; the presence, the absence, the risk, or the carrier status of the genetic or health condition; the one or more dog breeds; the one or more proportions of the one or more dog breeds; the family tree; the presence, the absence, the risk, or the carrier status of the phenotype or trait; and any combination thereof. In some embodiments, the method further comprises transmitting the report to a veterinarian.

In another aspect, the present disclosure provides a computer system for estimating a degree of ancestral relatedness between two individuals of a diploid population, comprising: a database that is configured to store haplotype data for a population of test individuals, the haplotype data comprising a plurality of genetic markers shared among the population of test individuals; and one or more computer processors operatively coupled to the database, wherein the one or more computer processors are individually or collectively programmed to: (a) divide the haplotype data into segments based on the plurality of genetic markers; (b) for each of the population of test individuals: (i) based on the plurality of genetic markers, match segments of the haplotype data that are identical-by-descent between a first individual and a second individual among the population of test individuals, each of the matched segments having a first size that is at least a pre-determined threshold size and comprising at least a pre-determined number of genetic markers; (ii) for each of the matched segments between the first individual and the second individual: divide the matched segment into a plurality of discrete genomic intervals; score each of the plurality of discrete genomic intervals based on (i) a degree of homozygosity matching of the discrete genomic interval within the first individual or the second individual or (ii) a degree of pairwise matching of the discrete genomic interval between the first individual and the second individual, thereby generating a plurality of scores; and correct the plurality of scores based on a consistency of the plurality of scores, thereby producing a plurality of corrected scores; and assign a plurality of weights to the plurality of discrete genomic intervals, based on the plurality of corrected scores of the discrete genomic intervals; and (iii) calculate a weighted sum over the plurality of discrete genomic intervals of the matched segment, based on the plurality of corrected scores and the plurality of weights; and (c) estimate the degree of ancestral relatedness between the first individual and the second individual based on the weighted sums of the matched segments.

In some embodiments, the diploid population is a mammal population. In some embodiments, the mammal population is a canine population, a feline population, a sport animal population, or a rodent population. In some embodiments, the mammal population is a canine population. In some embodiments, the canine population is a dog population. In some embodiments, the mammal population is a feline population. In some embodiments, the feline population is a cat population. In some embodiments, the mammal population is a sport animal population. In some embodiments, the sport animal population is a horse population. In some embodiments, the dog population comprises one or more dog breeds selected from the group consisting of: Affenpinscher, Afghan Hound, Africanis, Aidi, Airedale Terrier, Akbash Dog, Akita Inu, Alangu Mastiff, Alano Español, Alapaha Blue Blood Bulldog, Alaskan Klee Kai, Alaskan Malamute, Alaunt, Alopekis, Alpine Dachsbracke, Alsatian Shepalute, American Akita, American Bulldog, American Cocker Spaniel, American Eskimo Dog, American Foxhound, American Hairless Terrier, American Mastiff, American Pit Bull Terrier, American Staffordshire Terrier, American Water Spaniel, Anatolian Shepherd Dog, Anglo-Français de Petite Vénerie, Appenzeller Sennenhund, Argentine Dogo, Ariege Pointer, Ariegeois, Armant, Artois Hound, Australian Bulldog, Australian Cattle Dog, Australian Kelpie, Australian Shepherd, Australian Silky Terrier, Australian Stumpy Tail Cattle Dog, Australian Terrier, Austrian Black and Tan Hound, Austrian Pinscher, Azawakh, Bakharwal Dog, Barbet, Basenji, Basque Shepherd Dog, Basset Artésien Normand, Basset Bleu de Gascogne, Basset Fauve de Bretagne, Grand Basset Griffon Vendéen, Petit Basset Griffon Vendéen, Bavarian Mountain Hound, Beagle, Beagle-Harrier, Bearded Collie, Beauceron, Bedlington Terrier, Belgian Shepherd Dog, Belgian Shepherd Dog (Groenendael), Belgian Shepherd Dog (Laekenois), Belgian Shepherd Dog (Malinois), Belgian Shepherd (Tervuren), Bergamasco Shepherd, Berger Blanc Suisse, Berger Picard, Berner Laufhund, Bernese Mountain Dog, Bichon Frise, Billy, Bisben, Black and Tan Coonhound, Black and Tan Virginia Foxhound, Bullenbeisser, Black Norwegian Elkhound, Black Russian Terrier, Blackmouth Cur, Grand Bleu de Gascogne, Petit Bleu de Gascogne, Bloodhound, Blue Lacy, Blue Paul Terrier, Bluetick Coonhound, Boerboel, Bohemian Shepherd, Bolognese, Border Collie, Border Terrier, Borzoi, Bosnian Coarse-haired Hound, Boston Terrier, Bouvier des Ardennes, Bouvier des Flandres, Boxer, Boykin Spaniel, Bracco Italiano, Braque d'Auvergne, Braque du Bourbonnais, Braque du Puy, Braque Francais, Braque Saint-Germain, Brazilian Terrier, Briard, Briquet Griffon Vendéen, Brittany, Broholmer, Bruno Jura Hound, Bucovina Shepherd Dog, Bull and Terrier, Bull Terrier, Bull Terrier (Miniature), Bullmastiff, Bully Kutta, Cairn Terrier, Canaan Dog, Canadian Eskimo Dog, Canadian Pointer, Cane Corso, Cão da Serra de Aires, Cão de Castro Laboreiro, Cão Fila de Sao Miguel, Carolina Dog, Carpathian Shepherd Dog, Catahoula Cur, Catalan Sheepdog, Caucasian Shepherd Dog, Cavalier King Charles Spaniel, Central Asian Shepherd Dog, Cesky Fousek, Cesky Terrier, Polish Greyhound, Chesapeake Bay Retriever, Chien-gris, Chien Français Blanc et Noir, Chien Français Blanc et Orange, Chien Français Tricolore, Chihuahua, Chilean Fox Terrier, Chinese Chongqing Dog, Chinese Crested Dog, Chinese Imperial Dog, Chinook, Chippiparai, Chow Chow, Cimarrón Uruguayo, Cierny Sery, Cimeco dell'Etna, Clumber Spaniel, Rough Collie, Smooth Collie, Combai, Cordoba Fighting Dog, Coton de Tulear, Cretan Hound, Croatian Sheepdog, Cumberland Sheepdog, Curly Coated Retriever, Czechoslovakian Wolfdog, Dachshund, Dalmatian, Dandie Dinmont Terrier, Danish Swedish Farmdog, Dingo, Doberman Pinscher, Dogue de Bordeaux, Dogo Cubano, Dogo Guatemalteco, Dogo Sardesco, Drentse Patrijshond, Drever, Dunker, Dutch Shepherd Dog, Dutch Smoushond, East-European Shepherd, East Siberian Laika, Elo, English Cocker Spaniel, English Coonhound, English Foxhound, English Mastiff, English Pointer, English Setter, English Shepherd, English Springer Spaniel, English Toy Terrier (Black & Tan), English Water Spaniel, English White Terrier, Entlebucher Mountain Dog, Épagneul Bleu de Picardie, Estonian Hound, Estrela Mountain Dog, Eurasier, Field Spaniel, Fila Brasileiro, Findo, Finnish Hound, Finnish Lapphund, Finnish Spitz, Flat-Coated Retriever, Formosan Mountain Dog, Fox Terrier (Smooth), Wire Fox Terrier, French Brittany, French Bulldog, French Spaniel, Galgo Español, German Longhaired Pointer, German Pinscher, German Shepherd Dog, German Shorthaired Pointer, German Spaniel, German Spitz, German Wirehaired Pointer, Giant Schnauzer, Glen of Imaal Terrier, Golden Retriever, Gordon Setter, Grand Anglo-Français Blanc et Noir, Grand Anglo-Français Blanc et Orange, Grand Anglo-Français Tricolore, Grand Griffon Vendéen, Gran Mastin de Borínquen, Great Dane, Great Pyrenees, Greater Swiss Mountain Dog, Greenland Dog, Greyhound, Griffon Bleu de Gascogne, Griffon Bruxellois, Griffon Fauve de Bretagne, Griffon Nivemais, Gull Dong, Gull Terr, Hare Indian Dog, Hamiltonstövare, Hanover Hound, Harrier, Havanese, Hawaiian Poi Dog, Himalayan Sheepdog, Hokkaido, Hortaya Borzaya, Hovawart, Hungarian Hound, New Zealand Huntaway, Hygenhund, Ibizan Hound, Icelandic Sheepdog, Indian Spitz, Irish Bull Terrier, Irish Red and White Setter, Irish Setter, Irish Staffordshire Bull Terrier, Irish Terrier, Irish Water Spaniel, Irish Wolfhound, Istrian Shorthaired Hound, Istrian Coarse-haired Hound, Italian Greyhound, Jack Russell Terrier, Jagdterrier, Jämthund, Japanese Chin, Japanese Spitz, Japanese Terrier, Jonangi, Kaikadi, Kai Ken, Kangal Dog, Kanni, Karakachan Dog, Karelian Bear Dog, Karst Shepherd, Keeshond, Kerry Beagle, Kerry Blue Terrier, King Charles Spaniel, King Shepherd, Kintamani, Kishu, Komondor, Kooikerhondje, Koolie, Korean Jindo Dog, Korean Mastiff, Kromfohrländer, Kunming Wolf-dog, Kuri, Kuvasz, Kyi-Leo, Labrador Husky, Labrador Retriever, Lagotto Romagnolo, Lakeland Terrier, Lancashire Heeler, Landseer, Lapponian Herder, Leonberger, Lhasa Apso, Lithuanian Hound, Longhaired Whippet, Lottatore Brindisino, Löwchen, Magyar Agár, Majestic Tree Hound, Maltese, Manchester Terrier, Maremma Sheepdog, McNab, Mexican Hairless Dog, Miniature Australian Shepherd, Miniature Fox Terrier, Miniature Pinscher, Miniature Schnauzer, Miniature Siberian Husky, Mioritic, Molossus, Montenegrin Mountain Hound, Moscow Watchdog, Moscow Water Dog, Mountain Cur, Mountain View Cur, Mucuchies, Mudi, Mudhol Hound, Large Münsterländer, Small Münsterländer, Murray River Curly Coated Retriever, Neapolitan Mastiff, Newfoundland, New Guinea Singing Dog, Norfolk Spaniel, Norfolk Terrier, Norrbottenspets, North Country Beagle, Northern Inuit Dog, Norwegian Buhund, Norwegian Elkhound, Norwegian Lundehund, Norwich Terrier, Nova Scotia Duck-Tolling Retriever, Old Danish Pointer, Old English Sheepdog, Old English Bulldog, Old English Terrier, Old German Shepherd Dog, Olde English Bulldogge, Otterhound, Pachon Navarro, Paisley Terrier, Papillon, Parson Russell Terrier, Patterdale Terrier, Pekingese, Perro de Presa Canario, Perro de Presa Mallorquin, Peruvian Hairless Dog, Phaléne, Pharaoh Hound, Picardy Spaniel, Plott Hound, Podenco Canario, Pointer, Polish Hound, Polish Hunting Dog, Polish Lowland Sheepdog, Polish Tatra Sheepdog, Pomeranian, Pont-Audemer Spaniel, Poodle, Porcelaine, Portuguese Podengo, Portuguese Pointer, Portuguese Water Dog, Pražský Krysařík, Pudelpointer, Pug, Puli, Pumi, Pungsan Dog, Pyrenean Mastiff, Pyrenean Shepherd, Rafeiro do Alentejo, Rajapalayam, Rampur Greyhound, Rastreador Brasileiro, Ratonero Bodeguero Andaluz, Rat Terrier, Redbone Coonhound, Rhodesian Ridgeback, Rottweiler, Russian Spaniel, Russkiy Toy, Russo-European Laika, Russell Terrier, Saarlooswolfhond, Sabueso Espanol, Sage Ashayeri, Sage Mazandarani, Sakhalin Husky, Saluki, Samoyed, Sapsali, Šarplaninac, Schapendoes, Schillerstövare, Schipperke, Old Croatian Sighthound, Giant Schnauzer, Miniature Schnauzer, Standard Schnauzer, Schweizer Laufhund, Schweizerischer Niederlaufhund, Scotch Collie, Scottish Deerhound, Scottish Terrier, Sealyham Terrier, Segugio Italiano, Seppala Siberian Sleddog, Serbian Hound, Serbian Tricolour Hound, Shar Pei, Shetland Sheepdog, Shiba Inu, Shih Tzu, Shikoku, Shiloh Shepherd Dog, Shirak, Siberian Husky, Silken Windhound, Sinhala Hound, Skye Terrier, Sloughi, Slovak Cuvac, Slovakian Rough-haired Pointer, Slovenský Kopov, Smålandsstövare, Small Greek Domestic Dog, Soft-Coated Wheaten Terrier, South Russian Ovcharka, Southern Hound, Spanish Mastiff, Spanish Water Dog, Spinone Italiano, Sporting Lucas Terrier, St. Bernard, St. John's Water Dog, Stabyhoun, Staffordshire Bull Terrier, Stephens Cur, Styrian Coarse-haired Hound, Sussex Spaniel, Swedish Lapphund, Swedish Vallhund, Swedish Beagle, Tahltan Bear Dog, Taigan, Tamaskan Dog, Teddy Roosevelt Terrier, Telomian, Tenterfield Terrier, Thai Bangkaew Dog, Thai Ridgeback, Tibetan Mastiff, Tibetan Spaniel, Tibetan Terrier, Tomjak, Tosa, Toy Bulldog, Toy Fox Terrier, Toy Manchester Terrier, Treeing Cur, Treeing Walker Coonhound, Tyrolean Hound, Utonagan, Vizsla, Volpino Italiano, Weimaraner, Cardigan Welsh Corgi, Pembroke Welsh Corgi, Welsh Sheepdog, Welsh Springer Spaniel, Welsh Terrier, West Highland White Terrier, West Siberian Laika, Westphalian Dachsbracke, Wetterhoun, Whippet, White English Bulldog, White Shepherd Dog, Wirehaired Vizsla, Wirehaired Pointing Griffon, and Yorkshire Terrier. In some embodiments, the population comprises one or more purebred dogs (e.g., having a single breed type) or one or more mixed-breed dogs (e.g., having a plurality of breed types). In some embodiments, the population is a population of mixed-breed dogs having DNA from any number (e.g., 1, 2, 3, 4, 5, 6, 7, 8, 9, 10, or more than 10) or combination of the purebred dogs.

In some embodiments, the haplotype data is generated by processing genotype data of the population of test individuals using a haplotype phasing algorithm. In some embodiments, the haplotype phasing algorithm comprises a reference-based haplotype phasing algorithm. In some embodiments, the reference-based haplotype phasing algorithm comprises a Hidden Markov Model (HMM)-based search. In some embodiments, the reference-based haplotype phasing algorithm comprises an Eagle1 algorithm, an Eagle2 algorithm, a PHASE algorithm, a fastPHASE algorithm, a BEAGLE algorithm, a Findhap algorithm, an Impute algorithm, an FImpute algorithm, an AlphaImpute algorithm, an IMPUTE2 algorithm, a MaCH algorithm, a SHAPEIT1 algorithm, a SHAPEIT2 algorithm, a SHAPEIT3 algorithm, a SHAPEIT4 algorithm, or a combination thereof. In some embodiments, the haplotype phasing algorithm comprises a cohort-based haplotype phasing algorithm.

In some embodiments, the genotype data is obtained by assaying biological samples obtained from the population of test individuals. In some embodiments, the biological samples comprise blood samples, saliva samples, swab samples, cell samples, or tissue samples. In some embodiments, the assaying comprises sequencing the biological samples or derivatives thereof.

In some embodiments, the plurality of genetic markers comprises at least about 500, at least about 1,000, at least about 2,000, at least about 3,000, at least about 4,000, at least about 5,000, at least about 6,000, at least about 7,000, at least about 8,000, at least about 9,000, or at least about 10,000 distinct genetic markers.

In some embodiments, matching the segments of the haplotype data that are identical-by-descent comprises using a GERMLINE algorithm, a PLINK algorithm, a PREST algorithm, a Random Projection for IBD Detection (RaPID) algorithm, a Find IBD Shared Haplotypes Rapidly (FISHR) algorithm, a refined identical-by-descent (IBD) algorithm, a fastIBD algorithm, a KING algorithm, a HaploScore algorithm, a TRUFFLE algorithm, or a combination thereof. In some embodiments, the pre-determined threshold size is about 100 kilobase pairs (kbp), about 200 kbp, about 300 kbp, about 400 kbp, about 500 kbp, about 600 kbp, about 700 kbp, about 800 kbp, about 900 kbp, or about 1,000 kbp. In some embodiments, the pre-determined number of genetic markers is about 30, about 40, about 50, about 60, about 70, about 80, about 90, or about 100 distinct genetic markers.

In some embodiments, the one or more computer processors are individually or collectively programmed to further divide the matched segments such that the discrete genomic intervals of the plurality of discrete genomic intervals have an equal size. In some embodiments, the one or more computer processors are individually or collectively programmed to further divide the matched segments such that the discrete genomic intervals of the plurality of discrete genomic intervals have a variable size. In some embodiments, the variable size of a given discrete genomic interval of the plurality of discrete genomic intervals is determined based at least in part on a start position and an end position of IBD matches proximal to the given discrete genomic interval, a density of genetic markers in the given discrete genomic interval, a maximum number of markers for the given discrete genomic interval, a maximum length of the given discrete genomic interval, or a combination thereof.

In some embodiments, the one or more computer processors are individually or collectively programmed to further score each of the plurality of discrete genomic intervals based on (i) the degree of homozygosity matching of the discrete genomic interval within the first individual or the second individual and (ii) the degree of pairwise matching of the discrete genomic interval between the first individual and the second individual, thereby generating a plurality of homozygosity matching scores and a plurality of pairwise matching scores. In some embodiments, the one or more computer processors are individually or collectively programmed to further correct the plurality of pairwise matching scores based on a consistency of a given pairwise matching score with a corresponding homozygosity matching score, thereby producing a plurality of corrected pairwise matching scores.

In some embodiments, the one or more computer processors are individually or collectively programmed to further assign the plurality of weights to the plurality of discrete genomic intervals, based on a plurality of identity states for two alleles in two diploid individuals. In some embodiments, the plurality of identity states comprises identity states selected from Table 1, and the plurality of weights are assigned based on a plurality of contributions to relatedness $r_{xy}$ as listed in Table 1. In some embodiments, the degree of ancestral relatedness comprises a coefficient of relatedness. In some embodiments, the one or more computer processors are individually or collectively programmed to further calculate the weighted sum over the plurality of discrete genomic intervals of the matched segment, wherein the weighted sum is expressed by:

$$r_{xy} = \frac{\Delta 1 + \Delta 7 + (0.75 \times \Delta 3) + (0.5 \times \Delta 8)}{L}.$$

In some embodiments, the degree of ancestral relatedness comprises a coefficient of kinship. In some embodiments, the one or more computer processors are individually or collectively programmed to further calculate the weighted sum over the plurality of discrete genomic intervals of the matched segment, wherein the weighted sum is expressed by:

$$k_{xy} = \frac{\Delta 1 + (0.5 \times (\Delta 3 + \Delta 7)) + (0.25 \times \Delta 8)}{L}.$$

In some embodiments, estimating the degree of ancestral relatedness between the first individual and the second individual comprises determining a degree of inbreeding of the first individual or the second individual. In some embodiments, estimating the degree of ancestral relatedness between the first individual and the second individual comprises determining a degree of inbreeding of the first individual and the second individual. In some embodiments, the one or more computer processors are individually or collectively programmed to further determine a familial relationship between the first individual and the second individual based at least in part on the degree of inbreeding of the first individual and the second individual. In some embodiments, the familial relationship is a parent-child relationship, a sibling relationship, an aunt/uncle-nephew/niece relationship, a cousin relationship, a grandparent-grandchild relationship, or a great-grandparent-greatgrandchild relationship. In some embodiments, the familial relationship is given as a relationship between a pair of humans, such that the degree of ancestral relatedness between the first individual and the second individual is comparable to a degree of ancestral relatedness expected between the pair of humans. In some embodiments, the relationship is a parent-child relationship, a sibling relationship, an aunt/uncle-nephew/niece relationship, a cousin relationship, a grandparent-grandchild relationship, or a great-grandparent-greatgrandchild relationship.

In some embodiments, the one or more computer processors are individually or collectively programmed to further determine an expected degree of inbreeding of a potential offspring of the first individual and the second individual. In some embodiments, the one or more computer processors are individually or collectively programmed to further determine a recommendation indicative of whether or not to breed the first individual and the second individual together, based on the expected degree of inbreeding of the potential offspring of the first individual and the second individual. In some embodiments, the one or more computer processors are individually or collectively programmed to further determine a recommendation indicative of breeding the first individual and the second individual together, when the expected degree of inbreeding of the potential offspring of the first individual and the second individual does not exceed a pre-determined threshold degree of inbreeding. In some embodiments, the one or more computer processors are individually or collectively programmed to further determine a recommendation indicative of not breeding the first individual and the second individual together, when the expected degree of inbreeding of the potential offspring of the first individual and the second individual exceeds a pre-determined threshold degree of inbreeding. In some embodiments, the pre-determined threshold degree of inbreeding is about 0.10, about 0.15, about 0.20, about 0.25, about 0.30, about 0.35, about 0.40, about 0.45, or about 0.50.

In some embodiments, the one or more computer processors are individually or collectively programmed to further generate a social connection between a first person associated with the first individual and a second person associated with the second individual, based at least in part on the estimated degree of ancestral relatedness between the first individual and the second individual. In some embodiments, the social connection is generated when the estimated degree of ancestral relatedness between the first individual and the second individual exceeds a pre-determined threshold value. In some embodiments, the pre-determined threshold value is about 0.00001, about 0.0001, about 0.001, about 0.01, about 0.02, about 0.04, about 0.06, about 0.08, about 0.1, about 0.12, about 0.14, about 0.16, about 0.18, about 0.2, about 0.25, about 0.3, about 0.35, about 0.4, about 0.45, or about 0.5. In some embodiments, the social connection is generated through a social media network. In some embodiments, the first person is a pet owner of the first individual, and the second person is a pet owner of the second individual. In some embodiments, the same person is a pet owner of the first individual and the second individual. In some embodiments, generating the social connection between the first person and the second person comprises providing a location of the first person or the second person. In some embodiments, generating the social connection between the first person and the second person comprises providing a communication link between the first person and the second person.

In some embodiments, the one or more computer processors are individually or collectively programmed to further identify a familial relationship between the first individual and the second individual based at least in part on the degree of ancestral relatedness. In some embodiments, the familial relationship is a parent-child relationship, a sibling relationship, an aunt/uncle-nephew/niece relationship, a cousin relationship, a grandparent-grandchild relationship, or a great-grandparent-greatgrandchild relationship. In some embodiments, the familial relationship is given as a relationship between a pair of humans, such that the degree of ancestral relatedness between the first individual and the second individual is comparable to a degree of ancestral relatedness expected between the pair of humans. In some embodiments, the relationship is a parent-child relationship, a sibling relationship, an aunt/uncle-nephew/niece relationship, a cousin relationship, a grandparent-grandchild relationship, or a great-grandparent-greatgrandchild relationship.

In some embodiments, the one or more computer processors are individually or collectively programmed to further identify, for each of one or more individuals of the population of test individuals, a presence, an absence, a risk, or a carrier status of a genetic or health condition in the individual. In some embodiments, the genetic or health condition is selected from the group consisting of Thrombopathia (RASGRP2 Exon 8); Pyruvate Kinase Deficiency (PKLR Exon 7 Pug Variant); Factor IX Deficiency, Hemophilia B (F9 Exon 7, Terrier Variant); Pyruvate Kinase Deficiency (PKLR Exon 7 Beagle Variant); P2Y12 Receptor Platelet Disorder (P2RY12); Glanzmann's Thrombasthenia Type I (ITGA2B Exon 12); Von Willebrand Disease Type II, Type II vWD (VWF); May-Hegglin Anomaly (MYH9); Thrombopathia (RASGRP2 Exon 5, American Eskimo Dog Variant); Factor IX Deficiency, Hemophilia B (F9 Exon 7, Rhodesian Ridgeback Variant); Von Willebrand Disease Type I (VWF); Canine Elliptocytosis (SPTB Exon 30); Canine Leukocyte Adhesion Deficiency Type III, LAD3 (FERMT3); Prekallikrein Deficiency (KLKB1 Exon 8); Von Willebrand Disease Type III, Type III vWD (VWF Exon 4); Factor VIII Deficiency, Hemophilia A (F8 Exon 10, Boxer Variant); Trapped Neutrophil Syndrome (VPS13B); Pyruvate Kinase Deficiency (PKLR Exon 7 Labrador Variant); Thrombopathia (RASGRP2 Exon 5, Basset Hound Variant); Pyruvate Kinase Deficiency (PKLR Exon 5); Factor VIII Deficiency, Hemophilia A (F8 Exon 1, Shepherd Variant 2); Factor VII Deficiency (F7 Exon 5); Congenital Macrothrombocytopenia (TUBB1 Exon 1, Cavalier King Charles Spaniel Variant); Ligneous Membranitis, LM (PLG); Pyruvate Kinase Deficiency (PKLR Exon 10); Factor VIII Deficiency, Hemophilia A (F8 Exon 11, Shepherd Variant 1); Other Systems; Shar-Pei Autoinflammatory Disease, SPAID, Shar-Pei Fever (MTBP); Autosomal Recessive Amelogenesis Imperfecta, Familial Enamel Hypoplasia (Italian Greyhound Variant); Persistent Mullerian Duct Syndrome, PMDS (AMHR2); Deafness and Vestibular Syndrome of Dobermans, DVDob, DINGS; Eyes; Progressive Retinal Atrophy, crd2 (IQCB1); Primary Lens Luxation (ADAMTS17); Glaucoma Primary Open Angle Glaucoma (ADAMTS17 Exon 2); Progressive Retinal Atrophy, crd1 (PDE6B); Progressive Retinal Atrophy, rcd1 Rod-cone dysplasia, rcd1 (PDE6B Exon 21 Irish Setter Variant); Collie Eye Anomaly, Choroidal Hypoplasia, CEA (NHEJ1); Progressive Retinal Atrophy (SAG); Achromatopsia (CNGA3 Exon 7 German Shepherd Variant); Canine Multifocal Retinopathy cmr2 (BEST1 Exon 5); Glaucoma Primary Open Angle Glaucoma (ADAMTS17 Exon 11); Progressive Retinal Atrophy, prcd Progressive rod-cone degeneration (PRCD Exon 1); Hereditary Cataracts, Early-Onset Cataracts, Juvenile Cataracts (HSF4 Exon 9 Shepherd Variant); Autosomal Dominant Progressive Retinal Atrophy (RHO); Canine Multifocal Retinopathy cmr3 (BEST1 Exon 10 SNP); Achromatopsia (CNGA3 Exon 7 Labrador Retriever Variant); Canine Multifocal Retinopathy cmr1 (BEST1 Exon 2); Progressive Retinal Atrophy, rcd3 Rod-cone dysplasia, rcd3 (PDE6A); Progressive Retinal Atrophy (CNGB1); Golden Retriever Progressive Retinal Atrophy 2, GR-PRA2 (TTC8); Progressive Retinal Atrophy, CNGA (CNGA1 Exon 9); Golden Retriever Progressive Retinal Atrophy 1, GR-PRA1 (SLC4A3); Progressive Retinal Atrophy—crd4/cord1 (RPGRIP1); Congenital Stationary Night Blindness (RPE65); Macular Corneal Dystrophy, MCD (CHST6); Glaucoma Primary Open Angle Glaucoma (ADAMTS10 Exon 9); Canine Multifocal Retinopathy cmr3 (BEST1 Exon 10 Deletion); Glaucoma Primary Open Angle Glaucoma (ADAMTS10 Exon 17); Muscular; Centronuclear Myopathy (PTPLA); Myotonia Congenita (CLCN1 Exon 7); Inherited Myopathy of Great Danes (BIN1); Myotonia Congenita (CLCN1 Exon 23); Muscular Dystrophy Muscular Dystrophy (DMD Pembroke Welsh Corgi Variant); Exercise-Induced Collapse (DNM1); Muscular Dystrophy Muscular Dystrophy (DMD Golden Retriever Variant); Myostatin Deficiency, Bully Whippet Syndrome (MSTN); Myotubular Myopathy 1, X-linked Myotubular Myopathy, XL-MTM (MTM1, Labrador Variant); Muscular Dystrophy Cavalier King Charles Spaniel Variant 1; Multisystem; Primary Ciliary Dyskinesia, PCD (CCDC39 Exon 3); GM1 Gangliosidosis (GLB1 Exon 2); Mucopolysaccharidosis Type IIIA, Sanfilippo Syndrome Type A, MPS IIIA (SGSH Exon 6 Variant 1); Adult-Onset Neuronal Ceroid Lipofuscinosis (ATP13A2); GM1 Gangliosidosis (GLB1 Exon 15 Shiba Inu Variant); Neuronal Ceroid Lipofuscinosis 2, NCL 2 (TPP1 Exon 4); Mucopolysaccharidosis Type VII, Sly Syndrome, MPS VII (GUSB Exon 3); Canine Fucosidosis (FUCA1); GM1 Gangliosidosis (GLB1 Exon 15 Alaskan Husky Variant); Lagotto Storage Disease (ATG4D); Congenital Keratoconjunctivitis Sicca and Ichthyosiform Dermatosis, Dry Eye Curly Coat Syndrome, CKCSID (FAM83H Exon 5); Glycogen storage disease Type VII, Phosphofructokinase Deficiency, PFK Deficiency (PFKM Whippet and English Springer Spaniel Variant); Glycogen Storage Disease Type IA, Von Gierke Disease, GSD IA (G6PC); Glycogen storage disease Type VII, Phosphofructokinase Deficiency, PFK Deficiency (PFKM Wachtelhund Variant); Neuronal Ceroid Lipofuscinosis 1, NCL 1 (CLN5 Border Collie Variant); Neuronal Ceroid Lipofuscinosis 1, Cerebellar Ataxia, NCL-A (ARSG Exon 2); Neuronal Ceroid Lipofuscinosis 6, NCL 6 (CLN6 Exon 7); Mucopolysaccharidosis Type I, MPS I (IDUA); Renal Cystadenocarcinoma and Nodular Dermatofibrosis, RCND (FLCN Exon 7); Neuronal Ceroid Lipofuscinosis 10, NCL 10 (CTSD Exon 5); Globoid Cell Leukodystrophy, Krabbe disease (GALC Exon 5); Glycogen Storage Disease Type IIIA, GSD IIIA (AGL); Neuronal Ceroid Lipofuscinosis (MFSD8); GM2 Gangliosidosis (HEXB, Poodle Variant); X-linked Ectodermal Dysplasia, Anhidrotic Ectodermal Dysplasia (EDA Intron 8); Neuronal Ceroid Lipofuscinosis (CLN8 Australian Shepherd Variant); Neuronal Ceroid Lipofuscinosis 8, NCL 8 (CLN8 English Setter Variant); Neuronal Ceroid Lipofuscinosis 1, NCL 1 (PPT1 Exon 8); Neuronal Ceroid Lipofuscinosis (CLN5 Golden Retriever Variant); Mucopolysaccharidosis Type VII, Sly Syndrome, MPS VII (GUSB Exon 5); Glycogen Storage Disease Type II, Pompe's Disease, GSD II (GAA); GM2 Gangliosidosis (HEXA); Mucopolysaccharidosis Type IIIA, Sanfilippo Syndrome Type A, MPS IIIA (SGSH Exon 6 Variant 2); Skin & Connective Tissues; Ichthyosis (PNPLA1); Ichthyosis (SLC27A4); Dystrophic Epidermolysis Bullosa (COL7A1); Ichthyosis, Epidermolytic Hyperkeratosis (KRT10); Ectodermal Dysplasia, Skin Fragility Syndrome (PKP1); Ichthyosis (NIPAL4); Musladin-Lueke Syndrome (ADAMTSL2); Focal Non-Epidermolytic Palmoplantar Keratoderma, Pachyonychia Congenita (KRT16); Hereditary Nasal Parakeratosis (SUV39H2); Hereditary Footpad Hyperkeratosis (FAM83G); Brain and Spinal Cord; Juvenile-Onset Polyneuropathy, Leonberger Polyneuropathy 1, LPN1 (LPN1, ARHGEF10); Cerebellar Abiotrophy, Neonatal Cerebellar Cortical Degeneration, NCCD (SPTBN2); Narcolepsy (HCRTR2 Intron 6); L-2-Hydroxyglutaricaciduria, L2HGA (L2HGDH); Spongy Degeneration with Cerebellar Ataxia 2, SDCA2 (ATP1B2); Progressive Neuronal Abiotrophy, Canine Multiple System Degeneration, CMSD (SERACI Exon 15); Fetal-Onset Neonatal Neuroaxonal Dystrophy (MFN2); Neonatal Encephalopathy with Seizures, NEWS (ATF2); Benign Familial Juvenile Epilepsy, Remitting Focal Epilepsy (LGI2); Juvenile Laryngeal Paralysis and Polyneuropathy, Polyneuropathy with Ocular Abnormalities and Neuronal Vacuolation, POANV (RAB3GAP1, Rottweiler Variant); Progressive Neuronal Abiotrophy, Canine Multiple System Degeneration, CMSD (SERACI Exon 4); Cerebellar Ataxia, Progressive Early-Onset Cerebellar Ataxia (SEL1L); Hereditary Sensory Autonomic Neuropathy, Acral Mutilation Syndrome, AMS (GDNF-AS); Shaking Puppy Syndrome, X-linked Generalized Tremor Syndrome (PLP); Hypomyelination and Tremors (FNIP2); Spinocerebellar Ataxia, Late-Onset Ataxia, LoSCA (CAPN1); Polyneuropathy, NDRG1 Greyhound Variant (NDRG1 Exon 15); Polyneuropathy, NDRG1 Malamute Variant (NDRG1 Exon 4); Cerebellar Hypoplasia (VLDLR); Spongy Degeneration with Cerebellar Ataxia 1, SDCA1, SeSAME/EAST Syndrome (KCNJ10); Spinocerebellar Ataxia with Myokymia and/or Seizures (KCNJ10); Alaskan Husky Encephalopathy, Subacute Necrotizing Encephalomyelopathy (SLC19A3); Degenerative Myelopathy, DM (SOD1A); Alexander Disease (GFAP); Heart; Dilated Cardiomyopathy, DCM1 (PDK4); Long QT Syndrome (KCNQ1); Dilated Cardiomyopathy, DCM2 (TTN); Skeletal; Hereditary Vitamin D-Resistant Rickets (VDR); Osteogenesis Imperfecta, Brittle Bone Disease (COL1A1); Osteogenesis Imperfecta, Brittle Bone Disease (SERPINHI); Chondrodystrophy and Intervertebral Disc Disease, CDDY/IVDD, Type I IVDD (FGF4 retrogene—CFA12); Osteogenesis Imperfecta, Brittle Bone Disease (COL1A2); Craniomandibular Osteopathy, CMO (SLC37A2); Skeletal Dysplasia 2, SD2 (COL11A2); Cleft Lip and/or Cleft Palate (ADAMTS20); Oculoskeletal Dysplasia 1, Dwarfism-Retinal Dysplasia, OSD1 (COL9A3, Labrador Retriever); Osteochondrodysplasia, Skeletal Dwarfism (SLC13A1); Metabolic; Malignant Hyperthermia (RYRI); Hypocatalasia, Acatalasemia (CAT); Pyruvate Dehydrogenase Deficiency (PDP1); Kidney and Bladder; Hyperuricosuria and Hyperuricemia or Urolithiasis, HUU (SLC2A9); Polycystic Kidney Disease, PKD (PKD1); Protein Losing Nephropathy, PLN (NPHS1); Cystinuria Type II-A (SLC3A1); Primary Hyperoxaluria (AGXT); Cystinuria Type I-A (SLC3A1); Autosomal Recessive Hereditary Nephropathy, Familial Nephropathy, ARHN (COL4A4 Exon 3); X-Linked Hereditary Nephropathy, XLHN (COL4A5 Exon 35, Samoyed Variant 2); Cystinuria Type II-B (SLC7A9); 2,8-Dihydroxyadenine Urolithiasis, 2,8-DHA Urolithiasis (APRT); Neuromuscular; Episodic Falling Syndrome (BCAN); Congenital Myasthenic Syndrome (COLQ); Congenital Myasthenic Syndrome (CHAT); Immune; Severe Combined Immunodeficiency (RAG1); X-linked Severe Combined Immunodeficiency (IL2RG Variant 1); Severe Combined Immunodeficiency (PRKDC); X-linked Severe Combined Immunodeficiency (IL2RG Variant 2); Complement 3 Deficiency, C3 Deficiency (C3); Gastrointestinal; Imerslund-Grasbeck Syndrome, Selective Cobalamin Malabsorption (CUBN Exon 53); Imerslund-Grasbeck Syndrome, Selective Cobalamin Malabsorption (CUBN Exon 8); Clinical; MDR1 Drug Sensitivity (MDR1); Alanine Aminotransferase Activity (GPT); Hormones; and Congenital Hypothyroidism (TPO, Tenterfield Terrier Variant). In some embodiments, the risk is expressed as a probability or a relative risk of the individual having the genetic or health condition. In some embodiments, the relative risk is a numerical value (e.g., a relative risk ratio) or a categorical value (e.g., "at risk," "not at risk," or "clear"). In some embodiments, the carrier status is expressed as a positive or negative indication of the individual being a carrier of the genetic or health condition.

In some embodiments, the one or more computer processors are individually or collectively programmed to further identify, for each of one or more individuals of the population of test individuals, one or more dog breeds of the individual. In some embodiments, the one or more computer processors are individually or collectively programmed to further identify, for each of one or more individuals of the population of test individuals, one or more proportions of the one or more dog breeds of the individual. In some embodiments, the one or more computer processors are individually or collectively programmed to further generate a family tree of a plurality of individuals of the population of test individuals. In some embodiments, the one or more computer processors are individually or collectively programmed to further identify, for each of one or more individuals of the population of test individuals, a presence, absence, or risk of a phenotype or trait in the individual. In some embodiments, the phenotype or trait is selected from the group consisting of: base coat color (e.g., dark or light fur, color of pigment, and color dilution), color coat modifiers (e.g., hidden patterning, body pattern, and facial pattern), coat traits (e.g., furnishings, coat length, shedding, coat texture, hairlessness (Xolo type), hairlessness (Terrier type), and albinism), body features (e.g., muzzle length, tail length, hind dew claws, back muscling and bulk, and eye color), body size (e.g., smaller, intermediate, and larger), performance (e.g., altitude adaptation), genetic diversity (e.g., degree of inbreeding, and diversity in immune response).

In some embodiments, the one or more computer processors are individually or collectively programmed to further generate a report indicative of one or more of: the degree of ancestral relatedness; the familial relationship; the presence, the absence, the risk, or the carrier status of the genetic or health condition; the one or more dog breeds; the one or more proportions of the one or more dog breeds; the family tree; the presence, the absence, the risk, or the carrier status of the phenotype or trait; and any combination thereof. In some embodiments, the one or more computer processors are individually or collectively programmed to further transmit the report to a veterinarian.

In another aspect, the present disclosure provides a non-transitory computer readable medium comprising machine-executable code that, upon execution by one or more computer processors, implements a method for estimating a degree of ancestral relatedness between two individuals of a diploid population, the method comprising: (a) receiving haplotype data for a population of test individuals, the haplotype data comprising a plurality of genetic markers shared among the population of test individuals; (b) dividing the haplotype data into segments based on the plurality of genetic markers; (c) for each of the population of test individuals: (i) based on the plurality of genetic markers, matching segments of the haplotype data that are identical-by-descent between a first individual and a second individual among the population of test individuals, each of the matched segments having a first size that is at least a pre-determined threshold size and comprising at least a pre-determined number of genetic markers; (ii) for each of the matched segments between the first individual and the second individual: dividing the matched segment into a plurality of discrete genomic intervals; scoring each of the plurality of discrete genomic intervals based on (i) a degree of homozygosity matching of the discrete genomic interval within the first individual or the second individual or (ii) a degree of pairwise matching of the discrete genomic interval between the first individual and the second individual, thereby generating a plurality of scores; correcting the plurality of scores based on a consistency of the plurality of scores, thereby producing a plurality of corrected scores; and assigning a plurality of weights to the plurality of discrete genomic intervals, based on the plurality of corrected scores of the discrete genomic intervals; and (iii) calculating a weighted sum over the plurality of discrete genomic intervals of the matched segment, based on the plurality of corrected scores and the plurality of weights; and (d) estimating the degree of ancestral relatedness between the first individual and the second individual based on the weighted sums of the matched segments.

In some embodiments, the diploid population is a mammal population. In some embodiments, the mammal population is a canine population, a feline population, a sport animal population, or a rodent population. In some embodiments, the mammal population is a canine population. In some embodiments, the canine population is a dog population. In some embodiments, the mammal population is a feline population. In some embodiments, the feline population is a cat population. In some embodiments, the mammal population is a sport animal population. In some embodiments, the sport animal population is a horse population. In some embodiments, the dog population comprises one or more dog breeds selected from the group consisting of: Affenpinscher, Afghan Hound, Africanis, Aidi, Airedale Terrier, Akbash Dog, Akita Inu, Alangu Mastiff, Alano Español, Alapaha Blue Blood Bulldog, Alaskan Klee Kai, Alaskan Malamute, Alaunt, Alopekis, Alpine Dachsbracke, Alsatian Shepalute, American Akita, American Bulldog, American Cocker Spaniel, American Eskimo Dog, American Foxhound, American Hairless Terrier, American Mastiff, American Pit Bull Terrier, American Staffordshire Terrier, American Water Spaniel, Anatolian Shepherd Dog, Anglo-Français de Petite Vénerie, Appenzeller Sennenhund, Argentine Dogo, Ariege Pointer, Ariegeois, Armant, Artois Hound, Australian Bulldog, Australian Cattle Dog, Australian Kelpie, Australian Shepherd, Australian Silky Terrier, Australian Stumpy Tail Cattle Dog, Australian Terrier, Austrian Black and Tan Hound, Austrian Pinscher, Azawakh, Bakharwal Dog, Barbet, Basenji, Basque Shepherd Dog, Basset Artésien Normand, Basset Bleu de Gascogne, Basset Fauve de Bretagne, Grand Basset Griffon Vendéen, Petit Basset Griffon Vendéen, Bavarian Mountain Hound, Beagle, Beagle-Harrier, Bearded Collie, Beauceron, Bedlington Terrier, Belgian Shepherd Dog, Belgian Shepherd Dog (Groenendael), Belgian Shepherd Dog (Laekenois), Belgian Shepherd Dog (Malinois), Belgian Shepherd (Tervuren), Bergamasco Shepherd, Berger Blanc Suisse, Berger Picard, Berner Laufhund, Bernese Mountain Dog, Bichon Frisé, Billy, Bisben, Black and Tan Coonhound, Black and Tan Virginia Foxhound, Bullenbeisser, Black Norwegian Elkhound, Black Russian Terrier, Blackmouth Cur, Grand Bleu de Gascogne, Petit Bleu de Gascogne, Bloodhound, Blue Lacy, Blue Paul Terrier, Bluetick Coonhound, Boerboel, Bohemian Shepherd, Bolognese, Border Collie, Border Terrier, Borzoi, Bosnian Coarse-haired Hound, Boston Terrier, Bouvier des Ardennes, Bouvier des Flandres, Boxer, Boykin Spaniel, Bracco Italiano, Braque d'Auvergne, Braque du Bourbonnais, Braque du Puy, Braque Francais, Braque Saint-Germain, Brazilian Terrier, Briard, Briquet Griffon Vendéen, Brittany, Broholmer, Bruno Jura Hound, Bucovina Shepherd Dog, Bull and Terrier, Bull Terrier, Bull Terrier (Miniature), Bullmastiff, Bully Kutta, Cairn Terrier, Canaan Dog, Canadian Eskimo Dog, Canadian Pointer, Cane Corso, Cão da Serra de Aires, Cão de Castro Laboreiro, Cão Fila de Sao Miguel, Carolina Dog, Carpathian Shepherd Dog, Catahoula Cur, Catalan Sheepdog, Caucasian Shepherd Dog, Cavalier King Charles Spaniel, Central Asian Shepherd Dog, Cesky Fousek, Cesky Terrier, Polish Greyhound, Chesapeake Bay Retriever, Chien-gris, Chien Français Blanc et Noir, Chien Français Blanc et Orange, Chien Français Tricolore, Chihuahua, Chilean Fox Terrier, Chinese Chongqing Dog, Chinese Crested Dog, Chinese Imperial Dog, Chinook, Chippiparai, Chow Chow, Cimarrón Uruguayo, Cierny Sery, Cimeco dell'Etna, Clumber Spaniel, Rough Collie, Smooth Collie, Combai, Cordoba Fighting Dog, Coton de Tulear, Cretan Hound, Croatian Sheepdog, Cumberland Sheepdog, Curly Coated Retriever, Czechoslovakian Wolfdog, Dachshund, Dalmatian, Dandie Dinmont Terrier, Danish Swedish Farmdog, Dingo, Doberman Pinscher, Dogue de Bordeaux, Dogo Cubano, Dogo Guatemalteco, Dogo Sardesco, Drentse Patrijshond, Drever, Dunker, Dutch Shepherd Dog, Dutch Smoushond, East-European Shepherd, East Siberian Laika, Elo, English Cocker Spaniel, English Coonhound, English Foxhound, English Mastiff, English Pointer, English Setter, English Shepherd, English Springer Spaniel, English Toy Terrier (Black & Tan), English Water Spaniel, English White Terrier, Entlebucher Mountain Dog, Épagneul Bleu de Picardie, Estonian Hound, Estrela Mountain Dog, Eurasier, Field Spaniel, Fila Brasileiro, Findo, Finnish Hound, Finnish Lapphund, Finnish Spitz, Flat-Coated Retriever, Formosan Mountain Dog, Fox Terrier (Smooth), Wire Fox Terrier, French Brittany, French Bulldog, French Spaniel, Galgo Español, German Longhaired Pointer, German Pinscher, German Shepherd Dog, German Shorthaired Pointer, German Spaniel, German Spitz, German Wirehaired Pointer, Giant Schnauzer, Glen of Imaal Terrier, Golden Retriever, Gordon Setter, Grand Anglo-Français Blanc et Noir, Grand Anglo-Français Blanc et Orange, Grand Anglo-Français Tricolore, Grand Griffon Vendéen, Gran Mastin de Borínquen, Great Dane, Great Pyrenees, Greater Swiss Mountain Dog, Greenland Dog, Greyhound, Griffon Bleu de Gascogne, Griffon Bruxellois, Griffon Fauve de Bretagne, Griffon Nivemais, Gull Dong, Gull Terr, Hare Indian Dog, Hamiltonstövare, Hanover Hound, Harrier, Havanese, Hawaiian Poi Dog, Himalayan Sheepdog, Hokkaido, Hortaya Borzaya, Hovawart, Hungarian Hound, New Zealand Huntaway, Hygenhund, Ibizan Hound, Icelandic Sheepdog, Indian Spitz, Irish Bull Terrier, Irish Red and White Setter, Irish Setter, Irish Staffordshire Bull Terrier, Irish Terrier, Irish Water Spaniel, Irish Wolfhound, Istrian Shorthaired Hound, Istrian Coarse-haired Hound, Italian Greyhound, Jack Russell Terrier, Jagdterrier, Jämthund, Japanese Chin, Japanese Spitz, Japanese Terrier, Jonangi, Kaikadi, Kai Ken, Kangal Dog, Kanni, Karakachan Dog, Karelian Bear Dog, Karst Shepherd, Keeshond, Kerry Beagle, Kerry Blue Terrier, King Charles Spaniel, King Shepherd, Kintamani, Kishu, Komondor, Kooikerhondje, Koolie, Korean Jindo Dog, Korean Mastiff, Kromfohrländer, Kunming Wolf-dog, Kuri, Kuvasz, Kyi-Leo, Labrador Husky, Labrador Retriever, Lagotto Romagnolo, Lakeland Terrier, Lancashire Heeler, Landseer, Lapponian Herder, Leonberger, Lhasa Apso, Lithuanian Hound, Longhaired Whippet, Lottatore Brindisino, Löwchen, Magyar Agár, Majestic Tree Hound, Maltese, Manchester Terrier, Maremma Sheepdog, McNab, Mexican Hairless Dog, Miniature Australian Shepherd, Miniature Fox Terrier, Miniature Pinscher, Miniature Schnauzer, Miniature Siberian Husky, Mioritic, Molossus, Montenegrin Mountain Hound, Moscow Watchdog, Moscow Water Dog, Mountain Cur, Mountain View Cur, Mucuchies, Mudi, Mudhol Hound, Large Münsterländer, Small Münsterländer, Murray River Curly Coated Retriever, Neapolitan Mastiff, Newfoundland, New Guinea Singing Dog, Norfolk Spaniel, Norfolk Terrier, Norrbottenspets, North Country Beagle, Northern Inuit Dog, Norwegian Buhund, Norwegian Elkhound, Norwegian Lundehund, Norwich Terrier, Nova Scotia Duck-Tolling Retriever, Old Danish Pointer, Old English Sheepdog, Old English Bulldog, Old English Terrier, Old German Shepherd Dog, Olde English Bulldogge, Otterhound, Pachon Navarro, Paisley Terrier, Papillon, Parson Russell Terrier, Patterdale Terrier, Pekingese, Perro de Presa Canario, Perro de Presa Mallorquin, Peruvian Hairless Dog, Phaléne, Pharaoh Hound, Picardy Spaniel, Plott Hound, Podenco Canario, Pointer, Polish Hound, Polish Hunting Dog, Polish Lowland Sheepdog, Polish Tatra Sheepdog, Pomeranian, Pont-Audemer Spaniel, Poodle, Porcelaine, Portuguese Podengo, Portuguese Pointer, Portuguese Water Dog, Pražský Krysarík, Pudelpointer, Pug, Puli, Pumi, Pungsan Dog, Pyrenean Mastiff, Pyrenean Shepherd, Rafeiro do Alentejo, Rajapalayam, Rampur Greyhound, Rastreador Brasileiro, Ratonero Bodeguero Andaluz, Rat Terrier, Redbone Coonhound, Rhodesian Ridgeback, Rottweiler, Russian Spaniel, Russkiy Toy, Russo-European Laika, Russell Terrier, Saarlooswolfhond, Sabueso Espanol, Sage Ashayeri, Sage Mazandarani, Sakhalin Husky, Saluki, Samoyed, Sapsali, Šarplaninac, Schapendoes, Schillerstövare, Schipperke, Old Croatian Sighthound, Giant Schnauzer, Miniature Schnauzer, Standard Schnauzer, Schweizer Laufhund, Schweizerischer Niederlaufhund, Scotch Collie, Scottish Deerhound, Scottish Terrier, Sealyham Terrier, Segugio Italiano, Seppala Siberian Sleddog, Serbian Hound, Serbian Tricolour Hound, Shar Pei, Shetland Sheepdog, Shiba Inu, Shih Tzu, Shikoku, Shiloh Shepherd Dog, Shirak, Siberian Husky, Silken Windhound, Sinhala Hound, Skye Terrier, Sloughi, Slovak Cuvac, Slovakian Rough-haired Pointer, Slovenský Kopov, Smålandsstövare, Small Greek Domestic Dog, Soft-Coated Wheaten Terrier, South Russian Ovcharka, Southern Hound, Spanish Mastiff, Spanish Water Dog, Spinone Italiano, Sporting Lucas Terrier, St. Bernard, St. John's Water Dog, Stabyhoun, Staffordshire Bull Terrier, Stephens Cur, Styrian Coarse-haired Hound, Sussex Spaniel, Swedish Lapphund, Swedish Vallhund, Swedish Beagle, Tahltan Bear Dog, Taigan, Tamaskan Dog, Teddy Roosevelt Terrier, Telomian, Tenterfield Terrier, Thai Bangkaew Dog, Thai Ridgeback, Tibetan Mastiff, Tibetan Spaniel, Tibetan Terrier, Tomjak, Tosa, Toy Bulldog, Toy Fox Terrier, Toy Manchester Terrier, Treeing Cur, Treeing Walker Coonhound, Tyrolean Hound, Utonagan, Vizsla, Volpino Italiano, Weimaraner, Cardigan Welsh Corgi, Pembroke Welsh Corgi, Welsh Sheepdog, Welsh Springer Spaniel, Welsh Terrier, West Highland White Terrier, West Siberian Laika, Westphalian Dachsbracke, Wetterhoun, Whippet, White English Bulldog, White Shepherd Dog, Wirehaired Vizsla, Wirehaired Pointing Griffon, and Yorkshire Terrier. In some embodiments, the population comprises one or more purebred dogs (e.g., having a single breed type) or one or more mixed-breed dogs (e.g., having a plurality of breed types). In some embodiments, the population is a population of mixed-breed dogs having DNA from any number (e.g., 1, 2, 3, 4, 5, 6, 7, 8, 9, 10, or more than 10) or combination of the purebred dogs.

In some embodiments, the haplotype data is generated by processing genotype data of the population of test individuals using a haplotype phasing algorithm. In some embodiments, the haplotype phasing algorithm comprises a reference-based haplotype phasing algorithm. In some embodiments, the reference-based haplotype phasing algorithm comprises a Hidden Markov Model (HMM)-based search. In some embodiments, the reference-based haplotype phasing algorithm comprises an Eagle1 algorithm, an Eagle2 algorithm, a PHASE algorithm, a fastPHASE algorithm, a BEAGLE algorithm, a Findhap algorithm, an Impute algorithm, an FImpute algorithm, an AlphaImpute algorithm, an IMPUTE2 algorithm, a MaCH algorithm, a SHAPEIT1 algorithm, a SHAPEIT2 algorithm, a SHAPEIT3 algorithm, a SHAPEIT4 algorithm, or a combination thereof. In some embodiments, the haplotype phasing algorithm comprises a cohort-based haplotype phasing algorithm.

In some embodiments, the genotype data is obtained by assaying biological samples obtained from the population of test individuals. In some embodiments, the biological samples comprise blood samples, saliva samples, swab samples, cell samples, or tissue samples. In some embodiments, the assaying comprises sequencing the biological samples or derivatives thereof.

In some embodiments, the plurality of genetic markers comprises at least about 500, at least about 1,000, at least about 2,000, at least about 3,000, at least about 4,000, at least about 5,000, at least about 6,000, at least about 7,000, at least about 8,000, at least about 9,000, or at least about 10,000 distinct genetic markers.

In some embodiments, matching the segments of the haplotype data that are identical-by-descent comprises using a GERMLINE algorithm, a PLINK algorithm, a PREST algorithm, a Random Projection for IBD Detection (RaPID) algorithm, a Find IBD Shared Haplotypes Rapidly (FISHR) algorithm, a refined identical-by-descent (IBD) algorithm, a fastIBD algorithm, a KING algorithm, a HaploScore algorithm, a TRUFFLE algorithm, or a combination thereof. In some embodiments, the pre-determined threshold size is about 100 kilobase pairs (kbp), about 200 kbp, about 300 kbp, about 400 kbp, about 500 kbp, about 600 kbp, about 700 kbp, about 800 kbp, about 900 kbp, or about 1,000 kbp. In some embodiments, the pre-determined number of genetic markers is about 30, about 40, about 50, about 60, about 70, about 80, about 90, or about 100 distinct genetic markers.

In some embodiments, the method further comprises dividing the matched segments such that the discrete genomic intervals of the plurality of discrete genomic intervals have an equal size. In some embodiments, the method further comprises dividing the matched segments such that the discrete genomic intervals of the plurality of discrete genomic intervals have a variable size. In some embodiments, the variable size of a given discrete genomic interval of the plurality of discrete genomic intervals is determined based at least in part on a start position and an end position of IBD matches proximal to the given discrete genomic interval, a density of genetic markers in the given discrete genomic interval, a maximum number of markers for the given discrete genomic interval, a maximum length of the given discrete genomic interval, or a combination thereof.

In some embodiments, the method further comprises scoring each of the plurality of discrete genomic intervals based on (i) the degree of homozygosity matching of the discrete genomic interval within the first individual or the second individual and (ii) the degree of pairwise matching of the discrete genomic interval between the first individual and the second individual, thereby generating a plurality of homozygosity matching scores and a plurality of pairwise matching scores. In some embodiments, the method further comprises correcting the plurality of pairwise matching scores based on a consistency of a given pairwise matching score with a corresponding homozygosity matching score, thereby producing a plurality of corrected pairwise matching scores.

In some embodiments, the method further comprises assigning the plurality of weights to the plurality of discrete genomic intervals, based on a plurality of identity states for two alleles in two diploid individuals. In some embodiments, the plurality of identity states comprises identity states selected from Table 1, and the plurality of weights are assigned based on a plurality of contributions to relatedness $r_{xy}$ as listed in Table 1. In some embodiments, the degree of ancestral relatedness comprises a coefficient of relatedness. In some embodiments, the method further comprises calculating the weighted sum over the plurality of discrete genomic intervals of the matched segment, wherein the weighted sum is expressed by:

$$r_{xy} = \frac{\Delta 1 + \Delta 7 + (0.75 \times \Delta 3) + (0.5 \times \Delta 8)}{L}.$$

In some embodiments, the degree of ancestral relatedness comprises a coefficient of kinship. In some embodiments, the method further comprises calculating the weighted sum over the plurality of discrete genomic intervals of the matched segment, wherein the weighted sum is expressed by:

$$k_{xy} = \frac{\Delta 1 + (0.5 \times (\Delta 3 + \Delta 7)) + (0.25 \times \Delta 8)}{L}.$$

In some embodiments, estimating the degree of ancestral relatedness between the first individual and the second individual comprises determining a degree of inbreeding of the first individual or the second individual. In some embodiments, estimating the degree of ancestral relatedness between the first individual and the second individual comprises determining a degree of inbreeding of the first individual and the second individual. In some embodiments, the method further comprises determining a familial relationship between the first individual and the second individual based at least in part on the degree of inbreeding of the first individual and the second individual. In some embodiments, the familial relationship is a parent-child relationship, a sibling relationship, an aunt/uncle-nephew/niece relationship, a cousin relationship, a grandparent-grandchild relationship, or a great-grandparent-greatgrandchild relationship. In some embodiments, the familial relationship is given as a relationship between a pair of humans, such that the degree of ancestral relatedness between the first individual and the second individual is comparable to a degree of ancestral relatedness expected between the pair of humans. In some embodiments, the relationship is a parent-child relationship, a sibling relationship, an aunt/uncle-nephew/niece relationship, a cousin relationship, a grandparent-grandchild relationship, or a great-grandparent-greatgrandchild relationship.

In some embodiments, the method further comprises determining an expected degree of inbreeding of a potential offspring of the first individual and the second individual. In some embodiments, the method further comprises determining a recommendation indicative of whether or not to breed the first individual and the second individual together, based on the expected degree of inbreeding of the potential offspring of the first individual and the second individual. In some embodiments, the method further comprises determining a recommendation indicative of breeding the first individual and the second individual together, when the expected degree of inbreeding of the potential offspring of the first individual and the second individual does not exceed a pre-determined threshold degree of inbreeding. In some embodiments, the method further comprises determining a recommendation indicative of not breeding the first individual and the second individual together, when the expected degree of inbreeding of the potential offspring of the first individual and the second individual exceeds a pre-determined threshold degree of inbreeding. In some embodiments, the pre-determined threshold degree of inbreeding is about 0.10, about 0.15, about 0.20, about 0.25, about 0.30, about 0.35, about 0.40, about 0.45, or about 0.50.

In some embodiments, the method further comprises generating a social connection between a first person associated with the first individual and a second person associated with the second individual, based at least in part on the estimated degree of ancestral relatedness between the first individual and the second individual. In some embodiments, the social connection is generated when the estimated degree of ancestral relatedness between the first individual and the second individual exceeds a pre-determined threshold value. In some embodiments, the pre-determined threshold value is about 0.00001, about 0.0001, about 0.001, about 0.01, about 0.02, about 0.04, about 0.06, about 0.08, about 0.1, about 0.12, about 0.14, about 0.16, about 0.18, about 0.2, about 0.25, about 0.3, about 0.35, about 0.4, about 0.45, or about 0.5. In some embodiments, the social connection is generated through a social media network. In some embodiments, the first person is a pet owner of the first individual, and the second person is a pet owner of the second individual. In some embodiments, the same person is a pet owner of the first individual and the second individual. In some embodiments, generating the social connection between the first person and the second person comprises providing a location of the first person or the second person. In some embodiments, generating the social connection between the first person and the second person comprises providing a communication link between the first person and the second person.

In some embodiments, the method further comprises identifying a familial relationship between the first individual and the second individual based at least in part on the degree of ancestral relatedness. In some embodiments, the familial relationship is a parent-child relationship, a sibling relationship, an aunt/uncle-nephew/niece relationship, a cousin relationship, a grandparent-grandchild relationship, or a great-grandparent-greatgrandchild relationship. In some embodiments, the familial relationship is given as a relationship between a pair of humans, such that the degree of ancestral relatedness between the first individual and the second individual is comparable to a degree of ancestral relatedness expected between the pair of humans. In some embodiments, the relationship is a parent-child relationship, a sibling relationship, an aunt/uncle-nephew/niece relationship, a cousin relationship, a grandparent-grandchild relationship, or a great-grandparent-greatgrandchild relationship.

In some embodiments, the method further comprises identifying, for each of one or more individuals of the population of test individuals, a presence, an absence, a risk, or a carrier status of a genetic or health condition in the individual. In some embodiments, the genetic or health condition is selected from the group consisting of Thrombopathia (RASGRP2 Exon 8); Pyruvate Kinase Deficiency (PKLR Exon 7 Pug Variant); Factor IX Deficiency, Hemophilia B (F9 Exon 7, Terrier Variant); Pyruvate Kinase Deficiency (PKLR Exon 7 Beagle Variant); P2Y12 Receptor Platelet Disorder (P2RY12); Glanzmann's Thrombasthenia Type I (ITGA2B Exon 12); Von Willebrand Disease Type II, Type II vWD (VWF); May-Hegglin Anomaly (MYH9); Thrombopathia (RASGRP2 Exon 5, American Eskimo Dog Variant); Factor IX Deficiency, Hemophilia B (F9 Exon 7, Rhodesian Ridgeback Variant); Von Willebrand Disease Type I (VWF); Canine Elliptocytosis (SPTB Exon 30); Canine Leukocyte Adhesion Deficiency Type III, LAD3 (FERMT3); Prekallikrein Deficiency (KLKB1 Exon 8); Von Willebrand Disease Type III, Type III vWD (VWF Exon 4); Factor VIII Deficiency, Hemophilia A (F8 Exon 10, Boxer Variant); Trapped Neutrophil Syndrome (VPS13B); Pyruvate Kinase Deficiency (PKLR Exon 7 Labrador Variant); Thrombopathia (RASGRP2 Exon 5, Basset Hound Variant); Pyruvate Kinase Deficiency (PKLR Exon 5); Factor VIII Deficiency, Hemophilia A (F8 Exon 1, Shepherd Variant 2); Factor VII Deficiency (F7 Exon 5); Congenital Macrothrombocytopenia (TUBB1 Exon 1, Cavalier King Charles Spaniel Variant); Ligneous Membranitis, LM (PLG); Pyruvate Kinase Deficiency (PKLR Exon 10); Factor VIII Deficiency, Hemophilia A (F8 Exon 11, Shepherd Variant 1); Other Systems; Shar-Pei Autoinflammatory Disease, SPAID, Shar-Pei Fever (MTBP); Autosomal Recessive Amelogenesis Imperfecta, Familial Enamel Hypoplasia (Italian Greyhound Variant); Persistent Mullerian Duct Syndrome, PMDS (AMHR2); Deafness and Vestibular Syndrome of Dobermans, DVDob, DINGS; Eyes; Progressive Retinal Atrophy, crd2 (IQCB1); Primary Lens Luxation (ADAMTS17); Glaucoma Primary Open Angle Glaucoma (ADAMTS17 Exon 2); Progressive Retinal Atrophy, crd1 (PDE6B); Progressive Retinal Atrophy, rcd1 Rod-cone dysplasia, rcd1 (PDE6B Exon 21 Irish Setter Variant); Collie Eye Anomaly, Choroidal Hypoplasia, CEA (NHEJ1); Progressive Retinal Atrophy (SAG); Achromatopsia (CNGA3 Exon 7 German Shepherd Variant); Canine Multifocal Retinopathy cmr2 (BEST1 Exon 5); Glaucoma Primary Open Angle Glaucoma (ADAMTS17 Exon 11); Progressive Retinal Atrophy, prcd Progressive rod-cone degeneration (PRCD Exon 1); Hereditary Cataracts, Early-Onset Cataracts, Juvenile Cataracts (HSF4 Exon 9 Shepherd Variant); Autosomal Dominant Progressive Retinal Atrophy (RHO); Canine Multifocal Retinopathy cmr3 (BEST1 Exon 10 SNP); Achromatopsia (CNGA3 Exon 7 Labrador Retriever Variant); Canine Multifocal Retinopathy cmr1 (BEST1 Exon 2); Progressive Retinal Atrophy, rcd3 Rod-cone dysplasia, rcd3 (PDE6A); Progressive Retinal Atrophy (CNGB1); Golden Retriever Progressive Retinal Atrophy 2, GR-PRA2 (TTC8); Progressive Retinal Atrophy, CNGA (CNGA1 Exon 9); Golden Retriever Progressive Retinal Atrophy 1, GR-PRA1 (SLC4A3); Progressive Retinal Atrophy—crd4/cord1 (RPGRIP1); Congenital Stationary Night Blindness (RPE65); Macular Corneal Dystrophy, MCD (CHST6); Glaucoma Primary Open Angle Glaucoma (ADAMTS10 Exon 9); Canine Multifocal Retinopathy cmr3 (BEST1 Exon 10 Deletion); Glaucoma Primary Open Angle Glaucoma (ADAMTS10 Exon 17); Muscular; Centronuclear Myopathy (PTPLA); Myotonia Congenita (CLCN1 Exon 7); Inherited Myopathy of Great Danes (BIN1); Myotonia Congenita (CLCN1 Exon 23); Muscular Dystrophy Muscular Dystrophy (DMD Pembroke Welsh Corgi Variant); Exercise-Induced Collapse (DNM1); Muscular Dystrophy Muscular Dystrophy (DMD Golden Retriever Variant); Myostatin Deficiency, Bully Whippet Syndrome (MSTN); Myotubular Myopathy 1, X-linked Myotubular Myopathy, XL-MTM (MTM1, Labrador Variant); Muscular Dystrophy Cavalier King Charles Spaniel Variant 1; Multisystem; Primary Ciliary Dyskinesia, PCD (CCDC39 Exon 3); GM1 Gangliosidosis (GLB1 Exon 2); Mucopolysaccharidosis Type IIIA, Sanfilippo Syndrome Type A, MPS IIIA (SGSH Exon 6 Variant 1); Adult-Onset Neuronal Ceroid Lipofuscinosis (ATP13A2); GM1 Gangliosidosis (GLB1 Exon 15 Shiba Inu Variant); Neuronal Ceroid Lipofuscinosis 2, NCL 2 (TPP1 Exon 4); Mucopolysaccharidosis Type VII, Sly Syndrome, MPS VII (GUSB Exon 3); Canine Fucosidosis (FUCA1); GM1 Gangliosidosis (GLB1 Exon 15 Alaskan Husky Variant); Lagotto Storage Disease (ATG4D); Congenital Keratoconjunctivitis Sicca and Ichthyosiform Dermatosis, Dry Eye Curly Coat Syndrome, CKCSID (FAM83H Exon 5); Glycogen storage disease Type VII, Phosphofructokinase Deficiency, PFK Deficiency (PFKM Whippet and English Springer Spaniel Variant); Glycogen Storage Disease Type IA, Von Gierke Disease, GSD IA (G6PC); Glycogen storage disease Type VII, Phosphofructokinase Deficiency, PFK Deficiency (PFKM Wachtelhund Variant); Neuronal Ceroid Lipofuscinosis 1, NCL 1 (CLN5 Border Collie Variant); Neuronal Ceroid Lipofuscinosis 1, Cerebellar Ataxia, NCL-A (ARSG Exon 2); Neuronal Ceroid Lipofuscinosis 6, NCL 6 (CLN6 Exon 7); Mucopolysaccharidosis Type I, MPS I (IDUA); Renal Cystadenocarcinoma and Nodular Dermatofibrosis, RCND (FLCN Exon 7); Neuronal Ceroid Lipofuscinosis 10, NCL 10 (CTSD Exon 5); Globoid Cell Leukodystrophy, Krabbe disease (GALC Exon 5); Glycogen Storage Disease Type IIIA, GSD IIIA (AGL); Neuronal Ceroid Lipofuscinosis (MFSD8); GM2 Gangliosidosis (HEXB, Poodle Variant); X-linked Ectodermal Dysplasia, Anhidrotic Ectodermal Dysplasia (EDA Intron 8); Neuronal Ceroid Lipofuscinosis (CLN8 Australian Shepherd Variant); Neuronal Ceroid Lipofuscinosis 8, NCL 8 (CLN8 English Setter Variant); Neuronal Ceroid Lipofuscinosis 1, NCL 1 (PPT1 Exon 8); Neuronal Ceroid Lipofuscinosis (CLN5 Golden Retriever Variant); Mucopolysaccharidosis Type VII, Sly Syndrome, MPS VII (GUSB Exon 5); Glycogen Storage Disease Type II, Pompe's Disease, GSD II (GAA); GM2 Gangliosidosis (HEXA); Mucopolysaccharidosis Type IIIA, Sanfilippo Syndrome Type A, MPS IIIA (SGSH Exon 6 Variant 2); Skin & Connective Tissues; Ichthyosis (PNPLA1); Ichthyosis (SLC27A4); Dystrophic Epidermolysis Bullosa (COL7A1); Ichthyosis, Epidermolytic Hyperkeratosis (KRT10); Ectodermal Dysplasia, Skin Fragility Syndrome (PKP1); Ichthyosis (NIPAL4); Musladin-Lueke Syndrome (ADAMTSL2); Focal Non-Epidermolytic Palmoplantar Keratoderma, Pachyonychia Congenita (KRT16); Hereditary Nasal Parakeratosis (SUV39H2); Hereditary Footpad Hyperkeratosis (FAM83G); Brain and Spinal Cord; Juvenile-Onset Polyneuropathy, Leonberger Polyneuropathy 1, LPN1 (LPN1, ARHGEF10); Cerebellar Abiotrophy, Neonatal Cerebellar Cortical Degeneration, NCCD (SPTBN2); Narcolepsy (HCRTR2 Intron 6); L-2-Hydroxyglutaricaciduria, L2HGA (L2HGDH); Spongy Degeneration with Cerebellar Ataxia 2, SDCA2 (ATP1B2); Progressive Neuronal Abiotrophy, Canine Multiple System Degeneration, CMSD (SERACI Exon 15); Fetal-Onset Neonatal Neuroaxonal Dystrophy (MFN2); Neonatal Encephalopathy with Seizures, NEWS (ATF2); Benign Familial Juvenile Epilepsy, Remitting Focal Epilepsy (LGI2); Juvenile Laryngeal Paralysis and Polyneuropathy, Polyneuropathy with Ocular Abnormalities and Neuronal Vacuolation, POANV (RAB3GAP1, Rottweiler Variant); Progressive Neuronal Abiotrophy, Canine Multiple System Degeneration, CMSD (SERACI Exon 4); Cerebellar Ataxia, Progressive Early-Onset Cerebellar Ataxia (SEL1L); Hereditary Sensory Autonomic Neuropathy, Acral Mutilation Syndrome, AMS (GDNF-AS); Shaking Puppy Syndrome, X-linked Generalized Tremor Syndrome (PLP); Hypomyelination and Tremors (FNIP2); Spinocerebellar Ataxia, Late-Onset Ataxia, LoSCA (CAPN1); Polyneuropathy, NDRG1 Greyhound Variant (NDRG1 Exon 15); Polyneuropathy, NDRG1 Malamute Variant (NDRG1 Exon 4); Cerebellar Hypoplasia (VLDLR); Spongy Degeneration with Cerebellar Ataxia 1, SDCA1, SeSAME/EAST Syndrome (KCNJ10); Spinocerebellar Ataxia with Myokymia and/or Seizures (KCNJ10); Alaskan Husky Encephalopathy, Subacute Necrotizing Encephalomyelopathy (SLC19A3); Degenerative Myelopathy, DM (SOD1A); Alexander Disease (GFAP); Heart; Dilated Cardiomyopathy, DCM1 (PDK4); Long QT Syndrome (KCNQ1); Dilated Cardiomyopathy, DCM2 (TTN); Skeletal; Hereditary Vitamin D-Resistant Rickets (VDR); Osteogenesis Imperfecta, Brittle Bone Disease (COL1A1); Osteogenesis Imperfecta, Brittle Bone Disease (SERPINHI); Chondrodystrophy and Intervertebral Disc Disease, CDDY/IVDD, Type I IVDD (FGF4 retrogene—CFA12); Osteogenesis Imperfecta, Brittle Bone Disease (COL1A2); Craniomandibular Osteopathy, CMO (SLC37A2); Skeletal Dysplasia 2, SD2 (COL11A2); Cleft Lip and/or Cleft Palate (ADAMTS20); Oculoskeletal Dysplasia 1, Dwarfism-Retinal Dysplasia, OSD1 (COL9A3, Labrador Retriever); Osteochondrodysplasia, Skeletal Dwarfism (SLC13A1); Metabolic; Malignant Hyperthermia (RYRI); Hypocatalasia, Acatalasemia (CAT); Pyruvate Dehydrogenase Deficiency (PDP1); Kidney and Bladder; Hyperuricosuria and Hyperuricemia or Urolithiasis, HUU (SLC2A9); Polycystic Kidney Disease, PKD (PKD1); Protein Losing Nephropathy, PLN (NPHS1); Cystinuria Type II-A (SLC3A1); Primary Hyperoxaluria (AGXT); Cystinuria Type I-A (SLC3A1); Autosomal Recessive Hereditary Nephropathy, Familial Nephropathy, ARHN (COL4A4 Exon 3); X-Linked Hereditary Nephropathy, XLHN (COL4A5 Exon 35, Samoyed Variant 2); Cystinuria Type II-B (SLC7A9); 2,8-Dihydroxyadenine Urolithiasis, 2,8-DHA Urolithiasis (APRT); Neuromuscular; Episodic Falling Syndrome (BCAN); Congenital Myasthenic Syndrome (COLQ); Congenital Myasthenic Syndrome (CHAT); Immune; Severe Combined Immunodeficiency (RAG1); X-linked Severe Combined Immunodeficiency (IL2RG Variant 1); Severe Combined Immunodeficiency (PRKDC); X-linked Severe Combined Immunodeficiency (IL2RG Variant 2); Complement 3 Deficiency, C3 Deficiency (C3); Gastrointestinal; Imerslund-Grasbeck Syndrome, Selective Cobalamin Malabsorption (CUBN Exon 53); Imerslund-Grasbeck Syndrome, Selective Cobalamin Malabsorption (CUBN Exon 8); Clinical; MDR1 Drug Sensitivity (MDRT); Alanine Aminotransferase Activity (GPT); Hormones; and Congenital Hypothyroidism (TPO, Tenterfield Terrier Variant). In some embodiments, the risk is expressed as a probability or a relative risk of the individual having the genetic or health condition. In some embodiments, the relative risk is a numerical value (e.g., a relative risk ratio) or a categorical value (e.g., "at risk," "not at risk," or "clear"). In some embodiments, the carrier status is expressed as a positive or negative indication of the individual being a carrier of the genetic or health condition.

In some embodiments, the method further comprises identifying, for each of one or more individuals of the population of test individuals, one or more dog breeds of the individual. In some embodiments, the method further comprises identifying, for each of one or more individuals of the population of test individuals, one or more proportions of the one or more dog breeds of the individual. In some embodiments, the method further comprises generating a family tree of a plurality of individuals of the population of test individuals. In some embodiments, the method further comprises identifying, for each of one or more individuals of the population of test individuals, a presence, absence, or risk of a phenotype or trait in the individual. In some embodiments, the phenotype or trait is selected from the group consisting of: base coat color (e.g., dark or light fur, color of pigment, and color dilution), color coat modifiers (e.g., hidden patterning, body pattern, and facial pattern), coat traits (e.g., furnishings, coat length, shedding, coat texture, hairlessness (Xolo type), hairlessness (Terrier type), and albinism), body features (e.g., muzzle length, tail length, hind dew claws, back muscling and bulk, and eye color), body size (e.g., smaller, intermediate, and larger), performance (e.g., altitude adaptation), genetic diversity (e.g., degree of inbreeding, and diversity in immune response).

In some embodiments, the method further comprises generating a report indicative of one or more of: the degree of ancestral relatedness; the familial relationship; the presence, the absence, the risk, or the carrier status of the genetic or health condition; the one or more dog breeds; the one or more proportions of the one or more dog breeds; the family tree; the presence, the absence, the risk, or the carrier status of the phenotype or trait; and any combination thereof. In some embodiments, the method further comprises transmitting the report to a veterinarian.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
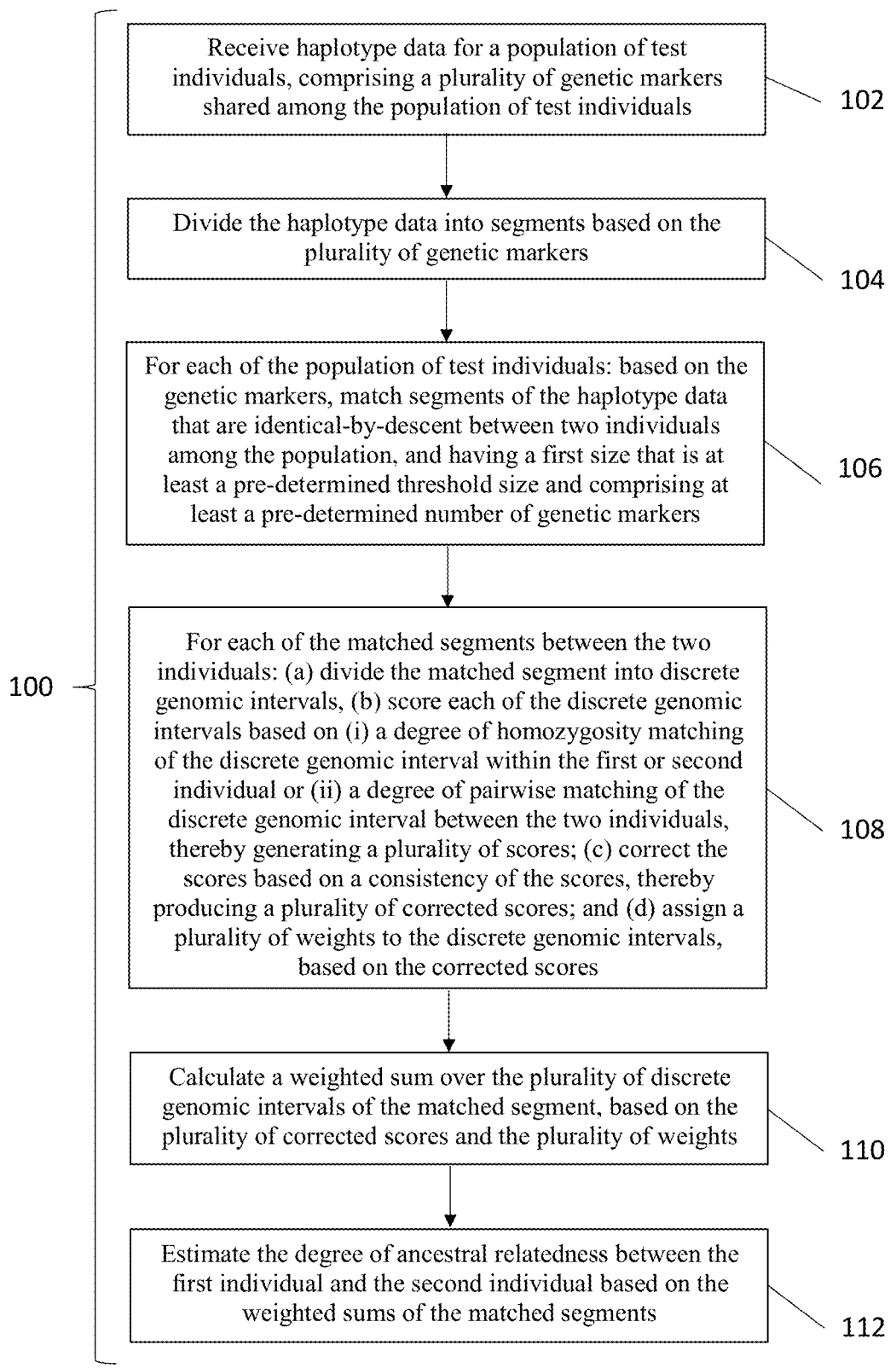
FIG. 1 illustrates an example method of estimating a degree of ancestral relatedness between two individuals of a diploid population, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular form "a", "an", and "the" include plural references unless the context clearly dictates otherwise. For example, the term "a sample" includes a plurality of samples, including mixtures thereof.

As used herein, the term "subject," generally refers to an entity or a medium that has testable or detectable genetic information. A subject can be a person, individual, or patient. A subject can be a vertebrate, such as, for example, a mammal. Non-limiting examples of mammals include humans, simians, farm animals, sport animals, rodents, and pets (e.g., canines such as dogs, or felines such as cats). The subject may have a normal or abnormal health or physiological state or condition or be suspected of having a normal or abnormal health or physiological state or condition. The subject may be displaying a symptom(s) indicative of a health or physiological state or condition. As an alternative, the subject can be asymptomatic with respect to such health or physiological state or condition.

The term "nucleic acid," or "polynucleotide," as used herein, generally refers to a molecule comprising one or more nucleic acid subunits, or nucleotides. A nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate (P03) groups. A nucleotide can include a nucleobase, a five-carbon sugar (either ribose or deoxyribose), and one or more phosphate groups, individually or in combination. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double stranded. A nucleic acid molecule may be linear, curved, or circular or any combination thereof.

The terms "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or ribonucleotides (RNA), or analogs thereof. A nucleic acid molecule can have a length of at least about 5 bases, 10 bases, 20 bases, 30 bases, 40 bases, 50 bases, 60 bases, 70 bases, 80 bases, 90, 100 bases, 110 bases, 120 bases, 130 bases, 140 bases, 150 bases, 160 bases, 170 bases, 180 bases, 190 bases, 200 bases, 300 bases, 400 bases, 500 bases, 1 kilobase (kb), 2 kb, 3, kb, 4 kb, 5 kb, 10 kb, or 50 kb or it may have any number of bases between any two of the aforementioned values. An oligonucleotide is typically composed of a specific sequence of four nucleotide bases: adenine (A); cytosine (C); guanine (G); and thymine (T) (uracil (U) for thymine (T) when the polynucleotide is RNA). Thus, the terms "nucleic acid molecule," "nucleic acid sequence," "nucleic acid fragment," "oligonucleotide" and "polynucleotide" are at least in part intended to be the alphabetical representation of a polynucleotide molecule. Alternatively, the terms may be applied to the polynucleotide molecule itself. This alphabetical representation can be input into databases in a computer having a central processing unit and/or used for bioinformatics applications such as functional genomics and homology searching. Oligonucleotides may include one or more nonstandard nucleotide(s), nucleotide analog(s) and/or modified nucleotides.

The term "sample," as used herein, generally refers to a biological sample. Examples of biological samples include nucleic acid molecules, amino acids, polypeptides, proteins, carbohydrates, fats, or viruses. In an example, a biological sample is a nucleic acid sample including one or more nucleic acid molecules. The biological sample may comprise or be derived from blood samples, saliva samples, swab samples, cell samples, or tissue samples. The nucleic acid molecules may be cell-free nucleic acid molecules, such as cell-free DNA (cfDNA) or cell-free RNA (cfRNA). The nucleic acid molecules may be derived from a variety of sources including human, mammal (e.g., dog), non-human mammal, ape, monkey, chimpanzee, reptilian, amphibian, or avian, sources. Further, samples may be extracted from a variety of animal fluids, including but not limited to bodily fluid samples such as blood, serum, plasma, vitreous, sputum, urine, tears, perspiration, saliva, semen, mucosal excretions, mucus, spinal fluid, cerebrospinal fluid (CSF), pleural fluid, peritoneal fluid, amniotic fluid, lymph fluid, and the like. Biological samples may be obtained or derived from subjects using an ethylenediaminetetraacetic acid (EDTA) collection tube, a cell-free RNA collection tube (e.g., Streck), or a cell-free DNA collection tube (e.g., Streck). Biological samples may be derived from whole blood samples by fractionation. Biological samples or derivatives thereof may contain cells. For example, a biological sample may be a blood sample or a derivative thereof (e.g., blood collected by a collection tube or blood drops) or a cell or tissue sample (e.g., a swab).

The term "whole blood," as used herein, generally refers to a blood sample that has not been separated into subcomponents (e.g., by centrifugation). The whole blood of a blood sample may contain cfDNA and/or germline DNA. Whole blood DNA (which may contain cfDNA and/or germline DNA) may be extracted from a blood sample. Whole blood DNA sequencing reads (which may contain cfDNA sequencing reads and/or germline DNA sequencing reads) may be extracted from whole blood DNA.

In an aspect, the present disclosure provides a computer-implemented method for estimating a degree of ancestral relatedness between two individuals of a diploid population, comprising: (a) receiving haplotype data for a population of test individuals, the haplotype data comprising a plurality of genetic markers shared among the population of test individuals; (b) dividing the haplotype data into segments based on the plurality of genetic markers; (c) for each of the population of test individuals: (i) based on the plurality of genetic markers, matching segments of the haplotype data that are identical-by-descent between a first individual and a second individual among the population of test individuals, each of the matched segments having a first size that is at least a pre-determined threshold size and comprising at least a pre-determined number of genetic markers; (ii) for each of the matched segments between the first individual and the second individual: dividing the matched segment into a plurality of discrete genomic intervals; scoring each of the plurality of discrete genomic intervals based on (i) a degree of homozygosity matching of the discrete genomic interval within the first individual or the second individual or (ii) a degree of pairwise matching of the discrete genomic interval between the first individual and the second individual, thereby generating a plurality of scores; correcting the plurality of scores based on a consistency of the plurality of scores, thereby producing a plurality of corrected scores; and assigning a plurality of weights to the plurality of discrete genomic intervals, based on the plurality of corrected scores of the discrete genomic intervals; and (iii) calculating a weighted sum over the plurality of discrete genomic intervals of the matched segment, based on the plurality of corrected scores and the plurality of weights; and (d) estimating the degree of ancestral relatedness between the first individual and the second individual based on the weighted sums of the matched segments.

FIG. 1 illustrates an example method 100 for estimating a degree of ancestral relatedness between two individuals of a diploid population, in accordance with some embodiments. In operation 102, the method 100 may comprise receiving haplotype data for a population of test individuals. For example, the haplotype data may comprise a plurality of genetic markers shared among the population of test individuals. Next, in operation 104, the method 100 may comprise dividing the haplotype data into segments based on the plurality of genetic markers. Next, in operation 106, for each of the population of test individuals, the method 100 may comprise, based on the plurality of genetic markers, matching segments of the haplotype data that are identical-by-descent between a first individual and a second individual among the population of test individuals. For example, each of the matched segments may have a first size that is at least a pre-determined threshold size and comprise at least a pre-determined number of genetic markers. Next, in operation 108, for each of the population of test individuals, the method 100 may comprise, for each of the matched segments between the first individual and the second individual: (a) dividing the matched segment into a plurality of discrete genomic intervals; (b) scoring each of the plurality of discrete genomic intervals, thereby generating a plurality of scores; (c) correcting the plurality of scores, thereby producing a plurality of corrected scores; and (d) assigning a plurality of weights to the plurality of discrete genomic intervals. In some embodiments, each of the plurality of discrete genomic intervals is scored based on (i) a degree of homozygosity matching of the discrete genomic interval within the first individual or the second individual, and/or (ii) a degree of pairwise matching of the discrete genomic interval between the first individual and the second individual. In some embodiments, the plurality of scores is corrected based on a consistency of the plurality of scores. In some embodiments, the plurality of weights is assigned to the plurality of discrete genomic intervals based on the plurality of corrected scores of the discrete genomic intervals.

In some embodiments, the method for estimating a degree of ancestral relatedness between two individuals of a diploid population may comprise calculating a coefficient of relationship (COR) between pairs of individuals (e.g., dogs) among a population. Based on the calculated COR values, a list may be generated for each individual in the population that comprises a list of the individual's closest genetic relatives. For example, such a list of relatives may be sorted by descending order of COR. Further, social network connections may be generated based on a COR between two related individuals (e.g., owners of related dogs).

Other methods of calculating COR values for dogs may use pedigrees, which may consist of a "family tree" mapping of a dog's ancestors and other relatives. Such methods may be limited at least because they cannot be used to estimate COR for dogs with no known pedigree information (e.g., rescue animals). Further, the use of pedigrees to calculate COR may also be problematic because accuracy may not be consistently high, the pedigrees may only provide a few generations of ancestry information, and because pedigrees may only be used to compute an "expected" relatedness (e.g., an amount of DNA that two individuals are expected to share based on their relationship). Generally, the actual relatedness of two individuals (e.g., dogs) may also depend on the random segregation and transmission of DNA through the family tree, and accurate calculation of relatedness may require identifying and tallying shared DNA tracts between animals. Although some methods may be used for phasing genotype data and identifying shared tracts between individuals, it may also be statistically difficult to distinguish tracts that are true identity by descent tracts from those that are statistical artifacts, to appropriately weight the tracts when calculating COR, and to handle noise in the data from structural variants and missing or low-quality markers.

Further, approaches for calculating COR between dogs is rendered more complex than in humans due to the much higher incidence of inbreeding in dogs than typical human populations. Recognizing this need, the present disclosure provides methods and systems for determining COR (e.g., between dogs) that takes inbreeding into account when determining the COR between two individuals. For example, a pair of two siblings in an outbred population may have a COR of approximately 0.5, as compared to another pair of two siblings in an inbred population that may have a COR of 0.7 or more. Using methods and systems of the present disclosure, the type of relationship between two individuals may be determined, even in cases where the individuals are part of inbred populations. For example, instead of determining that every pair of two dogs with a COR of 0.5 has a relatedness similar to that of full siblings, methods and systems of the present disclosure may be applied to distinguish between a first case in which a particular pair of dogs with a COR of 0.5 are full siblings vs. a second case in which another pair of dogs with a COR of 0.5 are related as uncle-niece from an inbred line.

Additionally, methods and systems of the present disclosure may be used to add a valuable social component to the genetic assay results of dogs. By allowing dog owners to directly connect with each other based on a relatedness of their pets, owners can gain more information from related dogs' owners about their own dog's history (e.g., which may be important or desirable information for owners of adopted dogs) and potential health risks for complex traits that are not part of the genetic assay (e.g., if a dog's sibling has a history of cancer, then the dog may gave a higher risk of cancer).

Methods and systems of the present disclosure may use one or more algorithms to determine a degree of ancestral relatedness (COR) between two individuals (e.g., of a diploid population). For example, the diploid population may be a mammal population (e.g., a canine population, a feline population, a sport animal population, or a rodent population). In some embodiments, the canine population is a dog population. In some embodiments, the dog population comprises one or more dog breeds selected from the group consisting of: Affenpinscher, Afghan Hound, Africanis, Aidi, Airedale Terrier, Akbash Dog, Akita Inu, Alangu Mastiff, Alano Español, Alapaha Blue Blood Bulldog, Alaskan Klee Kai, Alaskan Malamute, Alaunt, Alopekis, Alpine Dachsbracke, Alsatian Shepalute, American Akita, American Bulldog, American Cocker Spaniel, American Eskimo Dog, American Foxhound, American Hairless Terrier, American Mastiff, American Pit Bull Terrier, American Staffordshire Terrier, American Water Spaniel, Anatolian Shepherd Dog, Anglo-Français de Petite Vénerie, Appenzeller Sennenhund, Argentine Dogo, Ariege Pointer, Ariegeois, Armant, Artois Hound, Australian Bulldog, Australian Cattle Dog, Australian Kelpie, Australian Shepherd, Australian Silky Terrier, Australian Stumpy Tail Cattle Dog, Australian Terrier, Austrian Black and Tan Hound, Austrian Pinscher, Azawakh, Bakharwal Dog, Barbet, Basenji, Basque Shepherd Dog, Basset Artésien Normand, Basset Bleu de Gascogne, Basset Fauve de Bretagne, Grand Basset Griffon Vendéen, Petit Basset Griffon Vendéen, Bavarian Mountain Hound, Beagle, Beagle-Harrier, Bearded Collie, Beauceron, Bedlington Terrier, Belgian Shepherd Dog, Belgian Shepherd Dog (Groenendael), Belgian Shepherd Dog (Laekenois), Belgian Shepherd Dog (Malinois), Belgian Shepherd (Tervuren), Bergamasco Shepherd, Berger Blanc Suisse, Berger Picard, Berner Laufhund, Bernese Mountain Dog, Bichon Frisé, Billy, Bisben, Black and Tan Coonhound, Black and Tan Virginia Foxhound, Bullenbeisser, Black Norwegian Elkhound, Black Russian Terrier, Blackmouth Cur, Grand Bleu de Gascogne, Petit Bleu de Gascogne, Bloodhound, Blue Lacy, Blue Paul Terrier, Bluetick Coonhound, Boerboel, Bohemian Shepherd, Bolognese, Border Collie, Border Terrier, Borzoi, Bosnian Coarsehaired Hound, Boston Terrier, Bouvier des Ardennes, Bouvier des Flandres, Boxer, Boykin Spaniel, Bracco Italiano, Braque d'Auvergne, Braque du Bourbonnais, Braque du Puy, Braque Francais, Braque Saint-Germain, Brazilian Terrier, Briard, Briquet Griffon Vendéen, Brittany, Broholmer, Bruno Jura Hound, Bucovina Shepherd Dog, Bull and Terrier, Bull Terrier, Bull Terrier (Miniature), Bullmastiff, Bully Kutta, Cairn Terrier, Canaan Dog, Canadian Eskimo Dog, Canadian Pointer, Cane Corso, Cão da Serra de Aires, Cão de Castro Laboreiro, Cão Fila de Sao Miguel, Carolina Dog, Carpathian Shepherd Dog, Catahoula Cur, Catalan Sheepdog, Caucasian Shepherd Dog, Cavalier King Charles Spaniel, Central Asian Shepherd Dog, Cesky Fousek, Cesky Terrier, Polish Greyhound, Chesapeake Bay Retriever, Chien-gris, Chien Français Blanc et Noir, Chien Français Blanc et Orange, Chien Français Tricolore, Chihuahua, Chilean Fox Terrier, Chinese Chongqing Dog, Chinese Crested Dog, Chinese Imperial Dog, Chinook, Chippiparai, Chow Chow, Cimarrón Uruguayo, Cierny Sery, Cimeco dell'Etna, Clumber Spaniel, Rough Collie, Smooth Collie, Combai, Cordoba Fighting Dog, Coton de Tulear, Cretan Hound, Croatian Sheepdog, Cumberland Sheepdog, Curly Coated Retriever, Czechoslovakian Wolfdog, Dachshund, Dalmatian, Dandie Dinmont Terrier, Danish Swedish Farmdog, Dingo, Doberman Pinscher, Dogue de Bordeaux, Dogo Cubano, Dogo Guatemalteco, Dogo Sardesco, Drentse Patrijshond, Drever, Dunker, Dutch Shepherd Dog, Dutch Smoushond, East-European Shepherd, East Siberian Laika, Elo, English Cocker Spaniel, English Coonhound, English Foxhound, English Mastiff, English Pointer, English Setter, English Shepherd, English Springer Spaniel, English Toy Terrier (Black & Tan), English Water Spaniel, English White Terrier, Entlebucher Mountain Dog, Épagneul Bleu de Picardie, Estonian Hound, Estrela Mountain Dog, Eurasier, Field Spaniel, Fila Brasileiro, Findo, Finnish Hound, Finnish Lapphund, Finnish Spitz, Flat-Coated Retriever, Formosan Mountain Dog, Fox Terrier (Smooth), Wire Fox Terrier, French Brittany, French Bulldog, French Spaniel, Galgo Español, German Longhaired Pointer, German Pinscher, German Shepherd Dog, German Shorthaired Pointer, German Spaniel, German Spitz, German Wirehaired Pointer, Giant Schnauzer, Glen of Imaal Terrier, Golden Retriever, Gordon Setter, Grand Anglo-Français Blanc et Noir, Grand Anglo-Français Blanc et Orange, Grand Anglo-Français Tricolore, Grand Griffon Vendéen, Gran Mastin de Borínquen, Great Dane, Great Pyrenees, Greater Swiss Mountain Dog, Greenland Dog, Greyhound, Griffon Bleu de Gascogne, Griffon Bruxellois, Griffon Fauve de Bretagne, Griffon Nivemais, Gull Dong, Gull Terr, Hare Indian Dog, Hamiltonstövare, Hanover Hound, Harrier, Havanese, Hawaiian Poi Dog, Himalayan Sheepdog, Hokkaido, Hortaya Borzaya, Hovawart, Hungarian Hound, New Zealand Huntaway, Hygenhund, Ibizan Hound, Icelandic Sheepdog, Indian Spitz, Irish Bull Terrier, Irish Red and White Setter, Irish Setter, Irish Staffordshire Bull Terrier, Irish Terrier, Irish Water Spaniel, Irish Wolfhound, Istrian Shorthaired Hound, Istrian Coarse-haired Hound, Italian Greyhound, Jack Russell Terrier, Jagdterrier, Jämthund, Japanese Chin, Japanese Spitz, Japanese Terrier, Jonangi, Kaikadi, Kai Ken, Kangal Dog, Kanni, Karakachan Dog, Karelian Bear Dog, Karst Shepherd, Keeshond, Kerry Beagle, Kerry Blue Terrier, King Charles Spaniel, King Shepherd, Kintamani, Kishu, Komondor, Kooikerhondje, Koolie, Korean Jindo Dog, Korean Mastiff, Kromfohrländer, Kunming Wolf-dog, Kuri, Kuvasz, Kyi-Leo, Labrador Husky, Labrador Retriever, Lagotto Romagnolo, Lakeland Terrier, Lancashire Heeler, Landseer, Lapponian Herder, Leonberger, Lhasa Apso, Lithuanian Hound, Longhaired Whippet, Lottatore Brindisino, Löwchen, Magyar Agár, Majestic Tree Hound, Maltese, Manchester Terrier, Maremma Sheepdog, McNab, Mexican Hairless Dog, Miniature Australian Shepherd, Miniature Fox Terrier, Miniature Pinscher, Miniature Schnauzer, Miniature Siberian Husky, Mioritic, Molossus, Montenegrin Mountain Hound, Moscow Watchdog, Moscow Water Dog, Mountain Cur, Mountain View Cur, Mucuchies, Mudi, Mudhol Hound, Large Münsterländer, Small Münsterländer, Murray River Curly Coated Retriever, Neapolitan Mastiff, Newfoundland, New Guinea Singing Dog, Norfolk Spaniel, Norfolk Terrier, Norrbottenspets, North Country Beagle, Northern Inuit Dog, Norwegian Buhund, Norwegian Elkhound, Norwegian Lundehund, Norwich Terrier, Nova Scotia Duck-Tolling Retriever, Old Danish Pointer, Old English Sheepdog, Old English Bulldog, Old English Terrier, Old German Shepherd Dog, Olde English Bulldogge, Otterhound, Pachon Navarro, Paisley Terrier, Papillon, Parson Russell Terrier, Patterdale Terrier, Pekingese, Perro de Presa Canario, Perro de Presa Mallorquin, Peruvian Hairless Dog, Phaléne, Pharaoh Hound, Picardy Spaniel, Plott Hound, Podenco Canario, Pointer, Polish Hound, Polish Hunting Dog, Polish Lowland Sheepdog, Polish Tatra Sheepdog, Pomeranian, Pont-Audemer Spaniel, Poodle, Porcelaine, Portuguese Podengo, Portuguese Pointer, Portuguese Water Dog, Pražský Krysarík, Pudelpointer, Pug, Puli, Pumi, Pungsan Dog, Pyrenean Mastiff, Pyrenean Shepherd, Rafeiro do Alentejo, Rajapalayam, Rampur Greyhound, Rastreador Brasileiro, Ratonero Bodeguero Andaluz, Rat Terrier, Redbone Coonhound, Rhodesian Ridgeback, Rottweiler, Russian Spaniel, Russkiy Toy, Russo-European Laika, Russell Terrier, Saarlooswolfhond, Sabueso Espanol, Sage Ashayeri, Sage Mazandarani, Sakhalin Husky, Saluki, Samoyed, Sapsali, Šarplaninac, Schapendoes, Schillerstövare, Schipperke, Old Croatian Sighthound, Giant Schnauzer, Miniature Schnauzer, Standard Schnauzer, Schweizer Laufhund, Schweizerischer Niederlaufhund, Scotch Collie, Scottish Deerhound, Scottish Terrier, Sealyham Terrier, Segugio Italiano, Seppala Siberian Sleddog, Serbian Hound, Serbian Tricolour Hound, Shar Pei, Shetland Sheepdog, Shiba Inu, Shih Tzu, Shikoku, Shiloh Shepherd Dog, Shirak, Siberian Husky, Silken Windhound, Sinhala Hound, Skye Terrier, Sloughi, Slovak Cuvac, Slovakian Rough-haired Pointer, Slovenský Kopov, Smålandsstövare, Small Greek Domestic Dog, Soft-Coated Wheaten Terrier, South Russian Ovcharka, Southern Hound, Spanish Mastiff, Spanish Water Dog, Spinone Italiano, Sporting Lucas Terrier, St. Bernard, St. John's Water Dog, Stabyhoun, Staffordshire Bull Terrier, Stephens Cur, Styrian Coarse-haired Hound, Sussex Spaniel, Swedish Lapphund, Swedish Vallhund, Swedish Beagle, Tahltan Bear Dog, Taigan, Tamaskan Dog, Teddy Roosevelt Terrier, Telomian, Tenterfield Terrier, Thai Bangkaew Dog, Thai Ridgeback, Tibetan Mastiff, Tibetan Spaniel, Tibetan Terrier, Tomjak, Tosa, Toy Bulldog, Toy Fox Terrier, Toy Manchester Terrier, Treeing Cur, Treeing Walker Coonhound, Tyrolean Hound, Utonagan, Vizsla, Volpino Italiano, Weimaraner, Cardigan Welsh Corgi, Pembroke Welsh Corgi, Welsh Sheepdog, Welsh Springer Spaniel, Welsh Terrier, West Highland White Terrier, West Siberian Laika, Westphalian Dachsbracke, Wetterhoun, Whippet, White English Bulldog, White Shepherd Dog, Wirehaired Vizsla, Wirehaired Pointing Griffon, and Yorkshire Terrier. In some embodiments, the population comprises one or more purebred dogs (e.g., having a single breed type) or one or more mixed-breed dogs (e.g., having a plurality of breed types). In some embodiments, the population is a population of mixed-breed dogs having DNA from any number (e.g., 1, 2, 3, 4, 5, 6, 7, 8, 9, 10, or more than 10) or combination of the purebred dogs.

In some embodiments, a relatedness $r_{xy}$ may be calculated as a proportion of homologous alleles shared between 2 individuals due to identity-by-descent from common ancestor, and may be equal to 2 times the coefficient of kinship $f_{xy}$, assuming the individual is not in-bred. The coefficient of kinship may represent a probability that 2 alleles sampled from same locus in the 2 individuals are identical-by-descent. This may equal an inbreeding coefficient for potential offspring between two individuals x and y. However, in the case where the two individuals x and y are inbred, then the assumption that $r_{xy}=2*f_{xy}$ is not valid.

In some embodiments, a method for determining a degree of ancestral relatedness (COR) between two individuals is called WOOPHS (Weighted Observation of Pairwise Haplotype Sharing). In some embodiment, WOOPHS is configured to calculate an estimate of the coefficient of relationship (COR) between a test individual and other individuals in a genetic database. In some embodiments, WOOPHS is configured to calculate an expected degree of inbreeding of a prospective offspring of two individuals. The method may comprise receiving genotype data as inputs. For example, the genotype data may be obtained by assaying biological samples obtained from the population of test individuals. In some embodiments, the biological samples comprise blood samples, saliva samples, swab samples, cell samples (e.g., mouth or cheek swab), or tissue samples. In some embodiments, the assaying comprises sequencing the biological samples or derivatives thereof to generate the genotype data. For example, sequencing reads may be generated from the biological samples using any suitable sequencing method. The sequencing method can be a first-generation sequencing method, such as Maxam-Gilbert or Sanger sequencing, or a high-throughput sequencing (e.g., next-generation sequencing or NGS) method. A high-throughput sequencing method may sequence simultaneously (or substantially simultaneously) at least about 10,000, 100,000, 1 million, 10 million, 100 million, 1 billion, or more polynucleotide molecules. Sequencing methods may include, but are not limited to: pyrosequencing, sequencing-by-synthesis, single-molecule sequencing, nanopore sequencing, semiconductor sequencing, sequencing-by-ligation, sequencing-by-hybridization, Digital Gene Expression (Helicos), massively parallel sequencing, e.g., Helicos, Clonal Single Molecule Array (Solexa/Illumina), sequencing using PacBio, SOLiD, Ion Torrent, or Nanopore platforms.

In some embodiments, the sequencing comprises whole genome sequencing (WGS). The sequencing may be performed at a depth sufficient to generate the desired haplotype with a desired performance (e.g., accuracy, sensitivity, specificity, positive predictive value (PPV), negative predictive value (NPV), or the area under curve (AUC) of a receiver operator characteristic (ROC)). In some embodiments, the sequencing is performed at a depth of about 20×, about 30×, about 40×, about 50×, about 60×, about 70×, about 80×, about 90×, about 100×, about 150×, about 200×, about 250×, about 300×, about 350×, about 400×, about 450×, about 500×, or more than about 500×. In some embodiments, the sequencing is performed in a "low-pass" manner, for example, at a depth of no more than about 12×, no more than about 11×, no more than about 10×, no more than about 9×, no more than about 8×, no more than about 7×, no more than about 6×, no more than about 5×, no more than about 4×, no more than about 3.5×, no more than about 3×, no more than about 2.5×, no more than about 2×, no more than about 1.5×, or no more than about 1×.

In some embodiments, the sequencing reads may be aligned to a reference genome. The reference genome may comprise at least a portion of a genome (e.g., a dog genome or a human genome). The reference genome may comprise an entire genome (e.g., an entire dog genome or an entire human genome). The reference genome may comprise a database comprising a plurality of genomic regions that correspond to coding and/or non-coding genomic regions of a genome. The database may comprise a plurality of genomic regions that correspond to IBD coding and/or non-coding genomic regions of a genome, such as single nucleotide variants (SNVs), single nucleotide polymorphisms (SNPs), copy number variants (CNVs), insertions or deletions (indels), and fusion genes. The alignment may be performed using a Burrows-Wheeler algorithm or another alignment algorithm.

In some embodiments, quantitative measures of the sequencing reads may be generated for each of a plurality of genomic regions. Quantitative measures of the sequencing reads may be generated, such as counts of DNA sequencing reads that are aligned with a given genomic region. Sequencing reads having a portion or all of the sequencing read aligning with a given genomic region may be counted toward the quantitative measure for that genomic region. In some embodiments, genomic regions may comprise genetic markers such as IBD markers. Patterns of specific and non-specific genomic regions may be indicative of relatedness between individuals.

In some embodiments, measuring the plurality of counts of DNA sequencing reads comprises performing binding measurements of the plurality of DNA molecules at each of the plurality of genomic regions. In some embodiments, performing the binding measurements comprises assaying the plurality of DNA molecules using probes that are selective for at least a portion of the plurality of genomic regions in the plurality of DNA molecules. In some embodiments, the probes are nucleic acid molecules having sequence complementarity with nucleic acid sequences of the plurality of genomic regions. In some embodiments, the nucleic acid molecules are primers or enrichment sequences. In some embodiments, the assaying comprises use of array hybridization or polymerase chain reaction (PCR), or nucleic acid sequencing.

In some embodiments, the method further comprises enriching the plurality of DNA molecules for at least a portion of the plurality of genomic regions. In some embodiments, the enrichment comprises amplifying the plurality of DNA molecules. For example, the plurality of DNA molecules may be amplified by selective amplification (e.g., by using a set of primers or probes comprising nucleic acid molecules having sequence complementarity with nucleic acid sequences of the plurality of genomic regions). Alternatively or in combination, the plurality of DNA molecules may be amplified by universal amplification (e.g., by using universal primers). In some embodiments, the enrichment comprises selectively isolating at least a portion (e.g., mononucleotides and/or dinucleotides) of the plurality of DNA molecules.

In some embodiments, the counts of DNA sequencing reads may be normalized or corrected. For example, the counts of DNA sequencing reads may be normalized and/or corrected to account for known biases in sequencing and library preparation and/or known biases in sequencing and library preparation. In some embodiments, a subset of the quantitative measures or counts may be filtered out, e.g., based on a quality score of the sequencing reads.

The method for determining a degree of ancestral relatedness (COR) between two individuals may comprise using a phasing algorithm to process the genotype data to generate haplotype data. For example, this may be achieved by separating observed genotypes for a large number of single nucleotide polymorphisms (SNPs) shared across individuals along a chromosome into runs of haplotypes (e.g., alleles that likely occurred on same parental chromosome and have been inherited together). For example, the haplotype phasing algorithm may comprise a reference-based haplotype phasing algorithm (e.g., comprising a Hidden Markov Model (HMM)-based search). In some embodiments, the reference-based haplotype phasing algorithm comprises an Eagle1 algorithm, an Eagle2 algorithm, a PHASE algorithm, a fastPHASE algorithm, a BEAGLE algorithm, a Findhap algorithm, an Impute algorithm, an FImpute algorithm, an AlphaImpute algorithm, an IMPUTE2 algorithm, a MaCH algorithm, a SHAPEIT1 algorithm, a SHAPEIT2 algorithm, a SHAPEIT3 algorithm, a SHAPEIT4 algorithm, or a combination thereof. Alternatively, the haplotype phasing algorithm may comprise a cohort-based haplotype phasing algorithm.

In some embodiments, a method for determining a degree of ancestral relatedness (COR) between two individuals comprises processing the haplotype data to identify matching haplotypes, which are identical by descent (IBD), between a plurality of individuals in a population. For example, IBD haplotypes may be identified between all individuals among a population, or between a set of test individuals and a set of reference individuals. In some embodiments, matching haplotypes are identified when they meet a size threshold (e.g., greater than a size threshold, such as about 100 kilobase pairs (kbp), about 200 kbp, about 300 kbp, about 400 kbp, about 500 kbp, about 600 kbp, about 700 kbp, about 800 kbp, about 900 kbp, or about 1,000 kbp) and/or encompass a minimum threshold number of genetic markers (e.g., about 30, about 40, about 50, about 60, about 70, about 80, about 90, or about 100 distinct genetic markers). The identification of matching haplotypes may be performed using a GERMLINE algorithm (e.g., with the -haploid flag), a PLINK algorithm, a PREST algorithm, a Random Projection for IBD Detection (RaPID) algorithm, a Find IBD Shared Haplotypes Rapidly (FISHR) algorithm, a refined identical-by-descent (IBD) algorithm, a fastIBD algorithm, a KING algorithm, a HaploScore algorithm, a TRUFFLE algorithm, or a combination thereof.

In some embodiments, a method for determining a degree of ancestral relatedness (COR) between two individuals comprises using a match post-processing algorithm to take matching haplotypes between two individual dogs (e.g., dog A and dog B), including two haplotypes per dog (e.g., A.0, A.1, B.0, and B.1), and divide them into discrete genomic intervals.

In some embodiments, a method for determining a degree of ancestral relatedness (COR) between two individuals comprises, for each discrete genomic interval, scoring the states of all possible haplotype match types in the discrete genomic interval, and counting the numbers of such matches (yielding one or two scores per genomic interval). For example, matches may include "homozygosity" matches within a single dog (e.g. A.0|A.1) or "pairwise" matches between haplotypes in the two dogs (e.g. A.0|B.1). In some embodiments, the discrete genomic intervals are scored based on (i) the degree of homozygosity matching of the discrete genomic interval within the first individual or the second individual and (ii) the degree of pairwise matching of the discrete genomic interval between the first individual and the second individual, thereby generating a plurality of homozygosity matching scores and a plurality of pairwise matching scores.

In some embodiments, a method for determining a degree of ancestral relatedness (COR) between two individuals comprises correcting the plurality of pairwise matching scores based on a consistency of a given pairwise matching score with a corresponding homozygosity matching score, thereby producing a plurality of corrected pairwise matching scores. For example, the homozygosity matches may be used to "correct" or adjust the scoring of discrete genomic intervals with inconsistent or impossible numbers of pairwise matches. Because of inherent uncertainty in haplotype phase, haplotype matches within a dog may be more likely to represent true IBD than haplotype matches between two dogs. Therefore, WOOPHS may comprise using homozygosity matches to "correct" discrete genomic intervals with an inconsistent or impossible number of pairwise matches. For example, true matches may occur only in a limited number of ways. For example, if one and only one dog among a pair of dogs (A and B) is homozygous (e.g., A.0=A.1), then there may only be 2 or 4 pairwise matches (e.g., {A.0=A.1=B.0, or A.0=A.1=B.1}; or {A.0=A.1=B.0=B.1}). This correction may be performed to correct the scoring of all discrete intervals to be consistent with possible states.

In some embodiments, a method for determining a degree of ancestral relatedness (COR) between two individuals comprises assigning a plurality of weights to the plurality of discrete genomic intervals, based on a plurality of identity states for two alleles in two diploid individuals, and calculating a weighted sum of the genomic interval scores to yield the COR and/or COK. For example, weights may be determined for each discrete genomic interval for its partial contribution to relatedness and/or kinship (e.g., toward the coefficient of relatedness (COR) and/or coefficient of kinship (COK)). This may be performed according to an approach described by, for example, Hedrick and Lacy, J Hered., "Measuring relatedness between inbred individuals," 2015 January-February, 106(1): 20-5, which is incorporated herein by reference in its entirety. For example, the plurality of identity states may comprise identity states selected from Table 1, and the plurality of weights may be assigned based on a plurality of contributions to relatedness $r_{xy}$, as listed in Table 1. In some embodiments, the degree of ancestral relatedness comprises a coefficient of relatedness. For example, the weighted sum may be calculated over the plurality of discrete genomic intervals of the matched segment, such that the weighted sum is expressed by:

$$r_{xy} = \frac{\Delta 1 + \Delta 7 + (0.75 \times \Delta 3) + (0.5 \times \Delta 8)}{L}.$$

In some embodiments, the degree of ancestral relatedness comprises a coefficient of kinship. For example, the weighted sum may be calculated over the plurality of discrete genomic intervals of the matched segment, such that the weighted sum is expressed by.

$$k_{xy} = \frac{\Delta 1 + (0.5 \times (\Delta 3 + \Delta 7)) + (0.25 \times \Delta 8)}{L}.$$

| Identity state | Probability | Contribution to $f_{xy}$ | Contribution to $r_{xy}$ |
|---|---|---|---|
| a—b<br>\|  \|<br>c—d | $\Delta_1$ | 1 | 1 |
| a—b<br><br>c—d | $\Delta_2$ | 0 | 0 |
| a—b<br>/<br>c   d | $\Delta_3$ | 1/2 | 3/4 |
| a—b<br><br>c   d | $\Delta_4$ | 0 | 0 |
| a   b<br>/\|<br>c—d | $\Delta_5$ | 1/2 | 3/4 |
| a   b<br><br>c—d | $\Delta_6$ | 0 | 0 |
| a   b<br>\|  \|<br>c   d | $\Delta_7$ | 1/2 | 1 |

| Identity state | Probability | Contribution to $f_{xy}$ | Contribution to $r_{xy}$ |
|---|---|---|---|
| a—b<br>c d | $\Delta_8$ | 1/4 | 1/2 |
| a b<br>c d | $\Delta_9$ | 0 | 0 |

The 2 alleles in individual x are a and b and the 2 alleles in individual y are c and d. Horizontal lines indicate homozygosity in an individual from identity by descent. For the given identity states, the $\Delta_i$ values give the probability of identity-by-descent and the right 2 columns indicate the contribution to the inbreeding coefficient $f_{xy}$ of an offspring from the individuals x and y and relatedness $r_{xy}$ between individuals x and y.

Table 1: The 9 Identity States for the 2 Alleles in 2 Diploid Individuals where States Identical by Descent are Connected by a Line To summarize, the method for determining a degree of ancestral relatedness (COR) between two individuals may comprise identifying IBD tracts from phased data, scoring discrete genomic intervals based on observed pairwise haplotype match counts, performing pairwise match count correction based on homozygosity states at discrete genomic intervals, assigning weights to discrete tracts, and calculating a weighted sum to yield coefficient of relationship and/or coefficient of kinship scores.

Computer Systems

Figure 2:
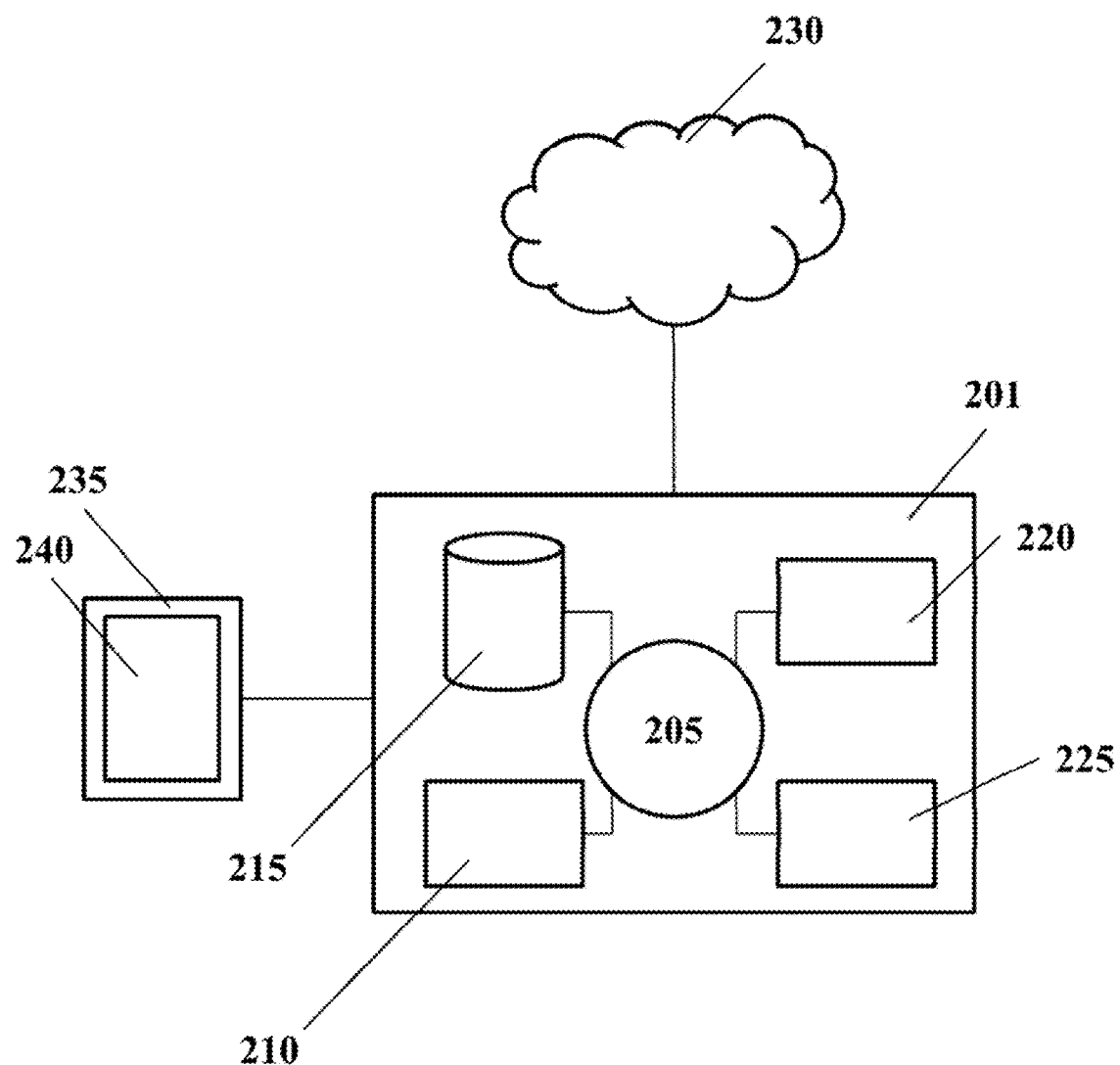
FIG. 2 illustrates a computer system that is programmed or otherwise configured to implement methods provided herein.

The present disclosure provides computer systems that are programmed to implement methods of the disclosure. FIG. 2 shows a computer system 201 that is programmed or otherwise configured to, for example, receive haplotype data for a population of test individuals (e.g., where the haplotype data comprises a plurality of genetic markers shared among the population of test individuals); divide haplotype data into segments based on the plurality of genetic markers; based on the plurality of genetic markers, match segments of the haplotype data that are identical-by-descent between a first individual and a second individual among the population of test individuals (e.g., where each of the matched segments has a first size that is at least a pre-determined threshold size and comprises at least a pre-determined number of genetic markers); divide matched segments into a plurality of discrete genomic intervals; score discrete genomic intervals based on (i) a degree of homozygosity matching of the discrete genomic interval within the first individual or the second individual or (ii) a degree of pairwise matching of the discrete genomic interval between the first individual and the second individual, thereby generating a plurality of scores; correct the plurality of scores based on a consistency of the plurality of scores, thereby producing a plurality of corrected scores; assign a plurality of weights to the plurality of discrete genomic intervals (e.g., based on the plurality of corrected scores of the discrete genomic intervals); calculate a weighted sum over the plurality of discrete genomic intervals of the matched segment (e.g., based on the plurality of corrected scores and the plurality of weights); and estimate the degree of ancestral relatedness between the first individual and the second individual (e.g., based on the weighted sums of the matched segments). The computer system 201 can regulate various aspects of analysis, calculation, and generation of the present disclosure, such as, for example, receiving haplotype data for a population of test individuals (e.g., where the haplotype data comprises a plurality of genetic markers shared among the population of test individuals); dividing haplotype data into segments based on the plurality of genetic markers; based on the plurality of genetic markers, matching segments of the haplotype data that are identical-by-descent between a first individual and a second individual among the population of test individuals (e.g., where each of the matched segments has a first size that is at least a pre-determined threshold size and comprises at least a pre-determined number of genetic markers); dividing matched segments into a plurality of discrete genomic intervals; score discrete genomic intervals based on (i) a degree of homozygosity matching of the discrete genomic interval within the first individual or the second individual or (ii) a degree of pairwise matching of the discrete genomic interval between the first individual and the second individual, thereby generating a plurality of scores; correcting the plurality of scores based on a consistency of the plurality of scores, thereby producing a plurality of corrected scores; assigning a plurality of weights to the plurality of discrete genomic intervals (e.g., based on the plurality of corrected scores of the discrete genomic intervals); calculating a weighted sum over the plurality of discrete genomic intervals of the matched segment (e.g., based on the plurality of corrected scores and the plurality of weights); and estimating the degree of ancestral relatedness between the first individual and the second individual (e.g., based on the weighted sums of the matched segments). The computer system 201 can be an electronic device of a user or a computer system that is remotely located with respect to the electronic device. The electronic device can be a mobile electronic device.

The computer system 201 includes a central processing unit (CPU, also "processor" and "computer processor" herein) 205, which can be a single core or multi core processor, or a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 are in communication with the CPU 205 through a communication bus (solid lines), such as a motherboard. The storage unit 215 can be a data storage unit (or data repository) for storing data. The computer system 201 can be operatively coupled to a computer network ("network") 230 with the aid of the communication interface 220. The network 230 can be the Internet, an internet and/or extranet, or an intranet and/or extranet that is in communication with the Internet. The network 230 in some cases is a telecommunication and/or data network. The network 230 can include one or more computer servers, which can enable distributed computing, such as cloud computing. For example, one or more computer servers may enable cloud computing over the network 230 ("the cloud") to perform various aspects of analysis, calculation, and generation of the present disclosure, such as, for example, receiving haplotype data for a population of test individuals (e.g., where the haplotype data comprises a plurality of genetic markers shared among the population of test individuals); dividing haplotype data into segments based on the plurality of genetic markers; based on the plurality of genetic markers, matching segments of the haplotype data that are identical-by-descent between a first individual and a second individual among the population of test individuals (e.g., where each of the matched segments has a first size that is at least a pre-determined threshold size and comprises at least a pre-determined number of genetic markers); dividing matched segments into a plurality of discrete genomic intervals; score discrete genomic intervals based on (i) a degree of homozygosity matching of the discrete genomic interval within the first individual or the second individual or (ii) a degree of pairwise matching of the discrete genomic interval between the first individual and the second individual, thereby generating a plurality of scores; correcting the plurality of scores based on a consistency of the plurality of scores, thereby producing a plurality of corrected scores; assigning a plurality of weights to the plurality of discrete genomic intervals (e.g., based on the plurality of corrected scores of the discrete genomic intervals); calculating a weighted sum over the plurality of discrete genomic intervals of the matched segment (e.g., based on the plurality of corrected scores and the plurality of weights); and estimating the degree of ancestral relatedness between the first individual and the second individual (e.g., based on the weighted sums of the matched segments). Such cloud computing may be provided by cloud computing platforms such as, for example, Amazon Web Services (AWS), Microsoft Azure, Google Cloud Platform, and IBM cloud. The network 230, in some cases with the aid of the computer system 201, can implement a peer-to-peer network, which may enable devices coupled to the computer system 201 to behave as a client or a server.

The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback.

The CPU 205 can be part of a circuit, such as an integrated circuit. One or more other components of the system 201 can be included in the circuit. In some cases, the circuit is an application specific integrated circuit (ASIC).

The storage unit 215 can store files, such as drivers, libraries and saved programs. The storage unit 215 can store user data, e.g., user preferences and user programs. The computer system 201 in some cases can include one or more additional data storage units that are external to the computer system 201, such as located on a remote server that is in communication with the computer system 201 through an intranet or the Internet.

The computer system 201 can communicate with one or more remote computer systems through the network 230. For instance, the computer system 201 can communicate with a remote computer system of a user (e.g., a pet owner, a kennel owner, a veterinarian, a breeder, an animal shelter employee, a physician, a nurse, a caretaker, a patient, or a subject). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 201 via the network 230.

Methods as described herein can be implemented by way of machine (e.g., computer processor) executable code stored on an electronic storage location of the computer system 201, such as, for example, on the memory 210 or electronic storage unit 215. The machine executable or machine readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 201 can include or be in communication with an electronic display 235 that comprises a user interface (UI) 240 for providing, for example, haplotype data, genetic markers, matched segments of the haplotype data that are identical-by-descent between a first individual and a second individual, scores of discrete genomic intervals, corrected scores of discrete genomic intervals, calculated weighted sums over a plurality of discrete genomic intervals, and an estimated degree of ancestral relatedness between the first individual and the second individual. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 205. The algorithm can, for example, receive haplotype data for a population of test individuals (e.g., where the haplotype data comprises a plurality of genetic markers shared among the population of test individuals); divide haplotype data into segments based on the plurality of genetic markers; based on the plurality of genetic markers, match segments of the haplotype data that are identical-by-descent between a first individual and a second individual among the population of test individuals (e.g., where each of the matched segments has a first size that is at least a pre-determined threshold size and comprises at least a pre-determined number of genetic markers); divide matched segments into a plurality of discrete genomic intervals; score discrete genomic intervals based on (i) a degree of homozygosity matching of the discrete genomic interval within the first individual or the second individual or (ii) a degree of pairwise matching of the discrete genomic interval between the first individual and the second individual, thereby generating a plurality of scores; correct the plurality of scores based on a consistency of the plurality of scores, thereby producing a plurality of corrected scores; assign a plurality of weights to the plurality of discrete genomic intervals (e.g., based on the plurality of corrected scores of the discrete genomic intervals); calculate a weighted sum over the plurality of discrete genomic intervals of the matched segment (e.g., based on the plurality of corrected scores and the plurality of weights); and estimate the degree of ancestral relatedness between the first individual and the second individual (e.g., based on the weighted sums of the matched segments). The computer system 201 can regulate various aspects of analysis, calculation, and generation of the present disclosure, such as, for example, receiving haplotype data for a population of test individuals (e.g., where the haplotype data comprises a plurality of genetic markers shared among the population of test individuals); dividing haplotype data into segments based on the plurality of genetic markers; based on the plurality of genetic markers, matching segments of the haplotype data that are identical-by-descent between a first individual and a second individual among the population of test individuals (e.g., where each of the matched segments has a first size that is at least a pre-determined threshold size and comprises at least a pre-determined number of genetic markers); dividing matched segments into a plurality of discrete genomic intervals; score discrete genomic intervals based on (i) a degree of homozygosity matching of the discrete genomic interval within the first individual or the second individual or (ii) a degree of pairwise matching of the discrete genomic interval between the first individual and the second individual, thereby generating a plurality of scores; correcting the plurality of scores based on a consistency of the plurality of scores, thereby producing a plurality of corrected scores; assigning a plurality of weights to the plurality of discrete genomic intervals (e.g., based on the plurality of corrected scores of the discrete genomic intervals); calculating a weighted sum over the plurality of discrete genomic intervals of the matched segment (e.g., based on the plurality of corrected scores and the plurality of weights); and estimating the degree of ancestral relatedness between the first individual and the second individual (e.g., based on the weighted sums of the matched segments).

EXAMPLES

Example 1: WOOPHS Algorithm for Assessing Degree of Relatedness or Kinship

Using methods and systems of the present disclosure, a Weighted Observation of Pairwise Haplotype Sharing (WOOPHS) algorithm is performed for assessing degree of relatedness or kinship between individuals (e.g., dogs). First, genotype data from a population of individuals is processed using GERMLINE to produce an array of pairwise and homozygous matches from the individuals. Then, for a given pair of individuals, the WOOPHS algorithm proceeds as follows. Match intervals (matches array) are sorted by chromosome, start position, and end position. Next, a zero-filled array (ibd scores) is created and initialized to store counts of pairwise and homozygous counts at discrete genomic intervals. Next, an empty list (prior intervals) is created and initialized to store all discrete genomic intervals until they are discarded. Next, for every chromosome: (a) a sorted array of all positions on the chromosome, denoted by discrete interval breaks (interval breaks), is generated and stored in a database; and (b) for every row (match row) in matches array on the chromosome: the current match row for any discrete intervals already encountered in prior rows is scored, any prior intervals that have been fully surpassed are deleted from memory, new discrete intervals in match row are created and stored, and new intervals are stored to prior intervals.

The scoring (based on match types and weights) and count correction/adjustment are performed as follows. The initial scoring of matched discrete genomic intervals is empirical. The number of pairwise matches between individuals (0, 1, 2, 3, or 4), or homozygosity matches within each individual (0 or 1) is recorded incrementally as the WOOPHS algorithm proceeds across discrete genomic intervals on a chromosome. However, in reality, there are a limited number of legitimate combinations of homozygous and pairwise matches. Because not all matches are necessarily reported by GERMLINE, depending on the specific flags used, the WOOPHS algorithm adjusts the observed counts to match legitimate count configurations (as shown by the summary of these possible count configurations in Table 1, reproduced from Hedrick and Lacy). Of the nine states in this table, only five contribute to relatedness and kinship, and two (states 3 and 5) can be further condensed as they are identical from the perspective of weight assignment. The remaining states can be ignored (e.g., assigned a weight of zero), since they do not contribute weight to the calculation of relatedness or kinship.

Therefore, WOOPHS operates on the following four match count state configurations:
(1) State 1={Pairwise=4, Homozygous=2}
(2) State 3={Pairwise=2, Homozygous=1}
(3) State 7={Pairwise=2, Homozygous=0}
(4) State 8={Pairwise=1, Homozygous=0}

Next, the WOOPHS algorithm comprises adjusting pairwise match counts in invalid match count state configurations as follows:

An observation of {Pairwise=3, Homozygous=1} is corrected to {Pairwise=2, Homozygous=1} (State 3).

An observation of {Pairwise=3, Homozygous=0} is corrected to {Pairwise=1, Homozygous=0} (State 8).

An observation of {Pairwise=4, Homozygous=0 or 1} is corrected to {Pairwise=2 (State 8 if Homozygous=0; State 7 if Homozygous=1).

An observation of {Pairwise=2, Homozygous=2} is corrected to {Pairwise=4} (State 1).

An observation of {Pairwise=1, Homozygous=1 or 2} is corrected to {Pairwise=2 (State 3 if Homozygous=1; Ignored if Homozygous=2).

An observation of {Pairwise=3, Homozygous=2} is corrected to {Pairwise=4 (State 1).

After the matched discrete genomic intervals are scored and corrected, the coefficient of relationship (COR) and/or the coefficient of kinship (COK) are calculated as follows. After pairwise match count state correction, all tracts are assigned weights for their contribution to relatedness and kinship, as indicated in Table 1. Finally, relatedness and kinship are calculated as follows. Let $\Delta i$ represent the sum total of the genome length assigned to one of the four match count states, i. Then the relatedness $r_{xy}$ and the kinship $k_{xy}$ may be calculated from the following expressions:

$$r_{xy} = \frac{\Delta 1 + \Delta 7 + (0.75 \times \Delta 3) + (0.5 \times \Delta 8)}{L}$$

$$k_{xy} = \frac{\Delta 1 + (0.5 \times (\Delta 3 + \Delta 7)) + (0.25 \times \Delta 8)}{L}$$

where L is the total length of the genome considered.

In some embodiments, the collected genotype data and/or haplotype data from the population of individuals may be stored in a database for future retrieval. Then, a sample may be collected from a test individual, then genotype data and haplotype data may be generated for the test individual. Next, the WOOPHS algorithm may be performed to generate a degree of relatedness or kinship between the test individual and each of one or more of the population of individuals. Finally, the database may be searched to retrieve a subset of the population of individuals having a degree of relatedness or kinship that exceeds a pre-determined threshold value. This subset of related individuals may be sorted or ranked based on the degree of relatedness or kinship to the test individual.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented method for estimating a degree of ancestral relatedness between two individuals of a diploid population, comprising:
   (a) receiving haplotype data for a population of test individuals, the haplotype data comprising a plurality of genetic markers shared among the population of test individuals, wherein the plurality of genetic markers comprises at least about 1,000 distinct genetic markers;
   (b) dividing the haplotype data into segments based on the plurality of genetic markers;
   (c) for each of the population of test individuals:
      (i) based on the plurality of genetic markers, matching segments of the haplotype data that are identical-by-descent (IBD) between a first individual and a second individual among the population of test individuals, each of the matched segments having a size that is at least about 100 kilobase pairs (kbp);
      (ii) for each of the matched segments between the first individual and the second individual:
         dividing the matched segment into a plurality of discrete genomic intervals;
         scoring each of the plurality of discrete genomic intervals based on (i) a degree of homozygosity matching of the discrete genomic interval within the first individual or the second individual, wherein the degree of homozygosity matching is a number of matching homozygous haplotypes within a discrete genomic interval within a single individual, and (ii) a degree of pairwise matching of the discrete genomic interval between the first individual and the second individual, wherein the degree of pairwise matching is a number of matching haplotypes within a discrete genomic interval between two individuals, thereby generating a plurality of scores;
         correcting each of the plurality of scores based on a consistency between degree of homozygosity matching and degree of pairwise matching of the plurality of scores, thereby producing a plurality of corrected scores; and
         assigning a plurality of weights to the plurality of discrete genomic intervals, based at least in part on the plurality of corrected scores; and
      (iii) calculating a weighted sum over the plurality of discrete genomic intervals of the matched segment, based on the plurality of corrected scores and the plurality of weights; and
   (d) estimating the degree of ancestral relatedness between the first individual and the second individual based on the weighted sums of the matched segments.

2. The method of claim 1, wherein the diploid population is a mammal population.

3. The method of claim 1, wherein the haplotype data is generated at least in part by processing genotype data of the population of test individuals using a haplotype phasing algorithm.

4. The method of claim 3, wherein the haplotype phasing algorithm comprises a reference-based haplotype phasing algorithm comprising a Hidden Markov Model (HMM)-based search.

5. The method of claim 3, further comprising obtaining the genotype data at least in part by assaying biological samples obtained from the population of test individuals or derivatives thereof.

6. The method of claim 5, wherein the assaying further comprises sequencing the biological samples or derivatives thereof to generate a plurality of sequencing reads.

7. The method of claim 1, wherein the plurality of genetic markers comprises at least about 10,000 distinct genetic markers.

8. The method of claim 1, wherein matching the segments of the haplotype data that are identical-by-descent comprises using a GERMLINE algorithm, a PLINK algorithm, a PREST algorithm, a Random Projection for IBD Detection (RaPID) algorithm, a Find IBD Shared Haplotypes Rapidly (FISHR) algorithm, a refined identical-by-descent (IBD) algorithm, a fastIBD algorithm, a KING algorithm, a HaploScore algorithm, a TRUFFLE algorithm, or a combination thereof.

9. The method of claim 1, wherein each of the matched segments has a size that is at least about 500 kilobase pairs (kbp).

10. The method of claim 1, wherein each of the matched segments comprises at least about 30 distinct genetic markers.

11. The method of claim 1, further comprising dividing the matched segments such that the discrete genomic intervals of the plurality of discrete genomic intervals have an equal size.

12. The method of claim 1, further comprising dividing the matched segments such that the discrete genomic intervals of the plurality of discrete genomic intervals have a variable size.

13. The method of claim 12, wherein the variable size of a given discrete genomic interval of the plurality of discrete genomic intervals is determined based at least in part on a start position and an end position of IBD matches proximal to the given discrete genomic interval, a density of genetic markers in the given discrete genomic interval, a maximum number of genetic markers for the given discrete genomic interval, a maximum length of the given discrete genomic interval, or a combination thereof.

14. The method of claim 1, further comprising correcting the plurality of pairwise matching scores based on a consistency of a given pairwise matching score with a corresponding homozygosity matching score, thereby producing a plurality of corrected pairwise matching scores.

15. The method of claim 1, further comprising assigning the plurality of weights to the plurality of discrete genomic intervals, based at least in part on a plurality of identity states for two alleles in two diploid individuals,
   wherein zero weights are assigned to discrete genomic intervals with identity states indicative of no pairwise matching between the two diploid individuals, and
   wherein non-zero weights are assigned only to discrete genomic intervals with identity states indicative of non-zero pairwise matching between the two diploid individuals.

16. The method of claim 15, wherein the plurality of identity states comprises identity states selected from the following:

| Identity state | Probability | Contribution to $f_{xy}$ | Contribution to $r_{xy}$ |
|---|---|---|---|
| a—b<br>c—d | $\Delta_1$ | 1 | 1 |
| a–b<br>c–d | $\Delta_2$ | 0 | 0 |
| a—b<br>c  d | $\Delta_3$ | $1/2$ | $3/4$ |
| a–b<br>c  d | $\Delta_4$ | 0 | 0 |
| a  b<br>c—d | $\Delta_5$ | $1/2$ | $3/4$ |
| a  b<br>c–d | $\Delta_6$ | 0 | 0 |
| a  b<br>c  d | $\Delta_7$ | $1/2$ | 1 |
| a  b<br>c  d | $\Delta_8$ | $1/4$ | $1/2$ |
| a  b<br>c  d | $\Delta_9$ | 0 | 0, | wherein the first individual x has alleles a and b,
   wherein the second individual y has alleles c and d,
   wherein the horizontal lines of the nine identity states indicate homozygosity in an individual from identity by descent, and
   wherein the plurality of weights are assigned further based on a plurality of contributions to the relatedness $r_{xy}$.

17. The method of claim 16, wherein the degree of ancestral relatedness comprises a coefficient of relatedness.

18. The method of claim 17, further comprising calculating the weighted sum over the plurality of discrete genomic intervals of the matched segment, wherein the weighted sum is expressed by:

$$r_{xy} = \frac{\Delta 1 + \Delta 7 + (0.75 \times \Delta 3) + (0.5 \times \Delta 8)}{L},$$

wherein $\Delta 1$, $\Delta 3$, $\Delta 7$, and $\Delta 8$ represent the sum total of the genome length assigned to one of the four match count states State 1, State 3, State 7, and State 8, respectively
   wherein State 1={Pairwise=4, Homozygous=2},
   wherein State 3={Pairwise=2, Homozygous=1},
   wherein State 7={Pairwise=2, Homozygous=0},
   wherein State 8={Pairwise=1, Homozygous=0}, and
   wherein L is the total length of the genome considered.

19. The method of claim 16, wherein the degree of ancestral relatedness comprises a coefficient of kinship that represents a probability that two alleles sampled from a same locus in the two individuals are identical-by-descent.

20. The method of claim 19, further comprising calculating the weighted sum over the plurality of discrete genomic intervals of the matched segment, wherein the weighted sum is expressed by:

$$k_{xy} = \frac{\Delta 1 + (0.5 \times (\Delta 3 + \Delta 7)) + (0.25 \times \Delta 8)}{L},$$

wherein $\Delta 1$, $\Delta 3$, $\Delta 7$, and $\Delta 8$ represent the sum total of the genome length assigned to one of the four match count states State 1, State 3, State 7, and State 8, respectively, wherein State 1={Pairwise=4, Homozygous=2}, wherein State 3={Pairwise=2, Homozygous=1}, wherein State 7={Pairwise=2, Homozygous=0}, wherein State 8={Pairwise=1, Homozygous=0}, and wherein L is the total length of the genome considered.

21. The method of claim 1, wherein estimating the degree of ancestral relatedness between the first individual and the second individual comprises determining a degree of inbreeding of the first individual or the second individual.

22. The method of claim 21, further comprising determining a familial relationship between the first individual and the second individual based at least in part on the degree of inbreeding of the first individual and the second individual.

23. The method of claim 22, wherein the familial relationship is a parent-child relationship, a sibling relationship, an aunt/uncle-nephew/niece relationship, a cousin relationship, or a grandparent-grandchild relationship.

24. The method of claim 1, further comprising generating a social connection between a first person associated with the first individual and a second person associated with the second individual, based at least in part on the estimated degree of ancestral relatedness between the first individual and the second individual.

25. The method of claim 1, further comprising identifying a familial relationship between the first individual and the second individual based at least in part on the degree of ancestral relatedness, wherein the familial relationship is a parent-child relationship, a sibling relationship, an aunt/uncle-nephew/niece relationship, a cousin relationship, or a grandparent-grandchild relationship.

26. A non-transitory computer readable medium comprising machine-executable code that, upon execution by one or more computer processors, implements a method for estimating a degree of ancestral relatedness between two individuals of a diploid population, the method comprising:
(a) receiving haplotype data for a population of test individuals, the haplotype data comprising a plurality of genetic markers shared among the population of test individuals, wherein the plurality of genetic markers comprises at least about 1,000 distinct genetic markers;
(b) dividing the haplotype data into segments based on the plurality of genetic markers;
(c) for each of the population of test individuals:
(i) based on the plurality of genetic markers, matching segments of the haplotype data that are identical-by-descent (IBD) between a first individual and a second individual among the population of test individuals, each of the matched segments having a size that is at least about 100 kilobase pairs (kbp);
(ii) for each of the matched segments between the first individual and the second individual:
dividing the matched segment into a plurality of discrete genomic intervals;
scoring each of the plurality of discrete genomic intervals based on (i) a degree of homozygosity matching of the discrete genomic interval within the first individual or the second individual, wherein the degree of homozygosity matching is a number of matching homozygous haplotypes within a discrete genomic interval within a single individual, and (ii) a degree of pairwise matching of the discrete genomic interval between the first individual and the second individual, wherein the degree of pairwise matching is a number of matching haplotypes within a discrete genomic interval between two individuals, thereby generating a plurality of scores;
correcting each of the plurality of scores based on a consistency between degree of homozygosity matching and degree of pairwise matching of the plurality of scores, thereby producing a plurality of corrected scores; and
assigning a plurality of weights to the plurality of discrete genomic intervals, based at least in part on the plurality of corrected scores; and
(iii) calculating a weighted sum over the plurality of discrete genomic intervals of the matched segment, based on the plurality of corrected scores and the plurality of weights; and
(d) estimating the degree of ancestral relatedness between the first individual and the second individual based on the weighted sums of the matched segments.

27. A computer system for estimating a degree of ancestral relatedness between two individuals of a diploid population, comprising:
a database that is configured to store haplotype data for a population of test individuals, the haplotype data comprising a plurality of genetic markers shared among the population of test individuals, wherein the plurality of genetic markers comprises at least about 1,000 distinct genetic markers; and
one or more computer processors operatively coupled to the database, wherein the one or more computer processors are individually or collectively programmed to:
(a) divide the haplotype data into segments based on the plurality of genetic markers;
(b) for each of the population of test individuals:
(i) based on the plurality of genetic markers, match segments of the haplotype data that are identical-by-descent (IBD) between a first individual and a second individual among the population of test individuals, each of the matched segments having a size that is at least about 100 kilobase pairs (kbp);
(ii) for each of the matched segments between the first individual and the second individual:
divide the matched segment into a plurality of discrete genomic intervals;
score each of the plurality of discrete genomic intervals based on (i) a degree of homozygosity matching of the discrete genomic interval within the first individual or the second individual, wherein the degree of homozygosity matching is a number of matching homozygous haplotypes within a discrete genomic interval within a single individual, and (ii) a degree of pairwise matching of the discrete genomic interval between the first individual and the second individual, wherein the degree of pairwise matching is a number of matching haplotypes within a discrete genomic interval between two individuals, thereby generating a plurality of scores;

correct each of the plurality of scores based on a consistency between degree of homozygosity matching and degree of pairwise matching of the plurality of scores, thereby producing a plurality of corrected scores; and assign a plurality of weights to the plurality of discrete genomic intervals, based at least in part on the plurality of corrected scores; and (iii) calculate a weighted sum over the plurality of discrete genomic intervals of the matched segment, based on the plurality of corrected scores and the plurality of weights; and (c) estimate the degree of ancestral relatedness between the first individual and the second individual based on the weighted sums of the matched segments.

28. The method of claim 3, wherein the haplotype phasing algorithm comprises a reference-based haplotype phasing algorithm, wherein the reference-based haplotype phasing algorithm comprises an Eagle1 algorithm, an Eagle2 algorithm, a PHASE algorithm, a fastPHASE algorithm, a BEAGLE algorithm, a Findhap algorithm, an Impute algorithm, an FImpute algorithm, an AlphaImpute algorithm, an IMPUTE2 algorithm, a MaCH algorithm, a SHAPEIT1 algorithm, a SHAPEIT2 algorithm, a SHAPEIT3 algorithm, a SHAPEIT4 algorithm, or a combination thereof.

29. The method of claim 5, wherein the assaying further comprises use of array hybridization.

30. The method of claim 6, wherein the assaying further comprises aligning the plurality of sequencing reads to a reference genome.

* * * * *